US011713305B2

(12) United States Patent
Martins et al.

(10) Patent No.: US 11,713,305 B2
(45) Date of Patent: *Aug. 1, 2023

(54) ZINC SENSORS FOR IN VIVO IMAGING OF BETA-CELL FUNCTION BY MRI

(71) Applicant: The Board of Regents of the University of Texas System, Austin, TX (US)

(72) Inventors: Andre F. Martins, Plano, TX (US); Sara Chirayil, Plano, TX (US); Maria Veronica Clavijo Jordan, Dallas, TX (US); A. Dean Sherry, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1060 days.

This patent is subject to a terminal disclaimer.

(21) Appl. No.: 16/026,340

(22) Filed: Jul. 3, 2018

(65) Prior Publication Data

US 2019/0031640 A1    Jan. 31, 2019

Related U.S. Application Data

(60) Provisional application No. 62/528,276, filed on Jul. 3, 2017.

(51) Int. Cl.
| | | |
|---|---|---|
| C07D 401/14 | (2006.01) | |
| A61K 49/10 | (2006.01) | |
| A61B 5/00 | (2006.01) | |
| C07F 5/00 | (2006.01) | |
| G01R 33/56 | (2006.01) | |
| A61B 5/055 | (2006.01) | |

(52) U.S. Cl.
CPC ............ *C07D 401/14* (2013.01); *A61B 5/004* (2013.01); *A61B 5/055* (2013.01); *A61B 5/425* (2013.01); *A61B 5/4381* (2013.01); *A61K 49/106* (2013.01); *C07F 5/003* (2013.01); *G01R 33/5601* (2013.01)

(58) Field of Classification Search
CPC ............ A61K 2121/00; A61K 2123/00; A61K 49/00; A61K 49/106; C07D 401/14; C07F 5/003; G01R 33/5601; A61B 5/425; A61B 5/04; A61B 5/055; A61B 5/4381; A61B 5/004
USPC ............. 424/1.11, 1.65, 9.1, 9.2, 9.3; 534/7, 534/10–16
See application file for complete search history.

(56) References Cited

U.S. PATENT DOCUMENTS

| | | | |
|---|---|---|---|
| 10,207,013 B2 * | 2/2019 | Preihs .................. | A61K 49/106 |
| 11,097,017 B2 * | 8/2021 | Preihs .................. | A61B 5/055 |
| 2011/0009605 A1 | 1/2011 | De León-Rodriguez | |

FOREIGN PATENT DOCUMENTS

WO    WO 2015/142583    9/2015

OTHER PUBLICATIONS

Martins et al, J. Am. Chem. Soc., vol. 140, pp. 17456-17464 (Year: 2018).*
Yu et al, J. Am. Chem. Soc., vol. 137, pp. 14173-14179 (Year: 2015).*
Abujudeh et al., "Retrospective assessment of prevalence of nephrogenic systemic fibrosis (NSF) after implementation of a new guideline for the use of gadobenate dimeglumine as a sole contrast agent for magnetic resonance examination in renally impaired patients", *J. Magn. Reson. Imaging*, 30, 1335, 2009.
De León-Rodriguez et al., "A second generation MRI contrast agent for imaging zinc ions in vivo", *MedChemComm.*, 3(4):480-483, 2012.
De León-Rodriguez et al., "Imaging free zinc levels in vivo—What can be learned?", *Inorganica Chim. Acta.*, 393:12-23, 2012.
Esqueda et al., "A new gadolinium-based MRI zinc sensor", *J. Am. Chem. Soc.*, 131(32):11387-11391, 2009.
Gonzalez et al., "Water-exchange, electronic relaxation, and rotational dynamics of the MRI contrast agent [Gd(DTPA-BMA)(H$_2$O)] in aqueous solution: a variable pressure, temperature, and magnetic field oxygen-17 NMR study", *J. Phys. Chem.*, 98:53-59, 1994.
Jaszberenyi et al., "Fine-tuning water exchange on Gd$^{III}$ poly(amino carboxylates) by modulation of steric crowding", *Dalton Trans.*, 0(16):2713-2719, 2005.
Kallen et al., "Gadolinium-containing magnetic resonance imaging contrast and nephrogenic systemic fibrosis: a case-control study", *Am. J. Kidney Dis.*, 51, 966, 2008.
Laurent et al., "How to measure the transmetallation of a gadolinium complex", *Contrast Media Mol. Imaging*, 5:305-308, 2010.
Major et al., "Mechanisms of ZnII-Activated Magnetic Resonance Imaging Agents", *Inorg. Chem.*, 47(22):10788-10795, 2008.
Major et al., "The synthesis and in vitro testing of a zinc-activated MRI contrast agent", *Proc. Natl. Acad. Sci. USA*, 104(35):13881-13886, 2007.
Martins et al., "Associating a negatively charged GdDOTA-derivative to the Pittsburgh compound B for targeting Aβ amyloid aggregates", *J. Biol. Inorg. Chem.*, 21(1):83-99, 2015.
Martins et al., "Gd$^{3+}$ complexes conjugated to Pittsburgh compound B: potential MRI markers of β-amyloid plaques", *J. Biol. Inorg. Chem.*, 19:281-295, 2014.
Martins et al., "PiB-conjugated, metal-based imaging probes: multimodal approaches for the visualization of β-amyloid plaques", *ACS Med. Chem. Lett.*, 4(5):436-440, 2013.
Mishra et al., "Critical in vitro evaluation of responsive MRI contrast agents for calcium and zinc", *Chem. Eur. J.*, 17(5):1529-1537, 2011.
Powell et al., "Structural and Dynamic Parameters Obtained from $^{17}$O NMR, EPR, and NMRD Studies of Monomeric and Dimeric Gd$^{3+}$ Complexes of Interest in Magnetic Resonance Imaging: An Integrated and Theoretically Self-Consistent Approach", *J. Am. Chem. Soc.*, 118(39):9333-9346, 1996.

(Continued)

*Primary Examiner* — D. L. Jones
(74) *Attorney, Agent, or Firm* — Parker Highlander PLLC

(57) ABSTRACT

In some aspects, the present disclosure provides gadolinium based sensors which may be used to image zinc ions in vivo. In some embodiments, the compounds show appropriate reactivity with zinc ions while maintaining high relaxivity to achieve improved background relative to other sensors.

17 Claims, 8 Drawing Sheets

(56) References Cited

OTHER PUBLICATIONS

Reilly, "Risk for nephrogenic systemic fibrosis with gadoteridol (ProHance) in patients who are on long-term hemodialysis", *Clin. J. Am. Soc. Nephrol.*, 3 (3), 747, 2008.

Rofsky et al., "Nephrogenic Systemic Fibrosis: A Chemical Perspective", *Radiology*, 247, 608, 2008.

Stewart et al., "Interdomain zinc site on human albumin", *Proc. Natl. Acad. Sci. USA*, 100(7):3701-3706, 2003.

Wiginton et al., "Gadolinium-based contrast exposure, nephrogenic systemic fibrosis, and gadolinium detection in tissue", *Am J Roentgenol*, 190, 1060, 2008.

Yu et al., "Amplifying the sensitivity of zinc (II) responsive MRI contrast agents by altering water exchange rates", *J. Am. Chem. Soc.*, 137(44):14173-14179, 2015.

Zhang et al., "PARACEST agents: modulating MRI contrast via water proton exchange", *Acc. Chem. Res.*, 36(10):783-790, 2003.

\* cited by examiner

ZINC SENSORS FOR IN VIVO IMAGING OF BETA-CELL FUNCTION BY MRI

This application claims the benefit of priority to U.S. Provisional Application No. 62/528,276, filed on Jul. 3, 2017, the entire contents of which are hereby incorporated by reference.

BACKGROUND

This invention was made with government support under Grant No. RO1 DK095416 awarded by the National Institutes of Health. The government has certain rights in the invention. Additionally, this invention was supported by the Robert A. Welch Foundation under Grant No. AT-0584.

1. FIELD

The present disclosure relates generally to the fields of diagnostic testing and imaging agents. The disclosure provides, for example, ligands for the preparation of MRI imaging agents, MRI imaging agents, compositions of the imaging agents, and methods of use thereof.

2. DESCRIPTION OF RELATED ART

Zinc(II) ions in particular are of particular interest as zinc is the second most abundant trace element in mammalian tissues and plays an extensive role in controlling gene transcription and metalloenzyme function (Esqueda, et al., 2009). The prostate, pancreas, and brain are known to contain relatively large amounts of zinc ions relative to other issues in the body. Zinc and the movement of zinc ions has been associated with the formation of β-amyloids, the release of insulin by β-cells in the pancreas and changes in concentration in zinc is associated with formation of tumors particular in prostate tissue. As such, a method of in vivo imaging of zinc represents a key goal to helping understand these biological functions and associated disease states such as Alzheimer's disease, diabetes, and cancer.

Esqueda, et al. (2009) and US Patent Application 2011/0009605 reported an MRI based zinc targeting contrast agent which contained two dipicolylamine units conjugated to a Gd-chelated DOTA. This ligand in the presence of zinc shows increased relaxivity compared to the ligand without zinc present. Unfortunately, this particular ligand still has relatively low relaxivity giving and therefore a relatively high (~100 μM) detection limit and thus improvements in the relaxivity of the complex can greatly improve the detection limit of the contrast agent which would be useful in a larger variety of biological applications. Additional compounds were described by Yu, et al. (2015) and PCT/US2015/019928 show high relaxivities and strong zinc binding but these particular molecules have several disadvantages. First, the high affinity for zinc ions results in poor background resolution of the zinc as the sensor binds to endogenous zinc ions, which resulting in physiological competition, rather than just the increased concentrations during insulin secretion. Additionally, the compounds also have overall positive charge and high kinetic stability. Therefore, there remains a need to develop new sensors which show improved chemical properties as well as appropriate zinc binding levels to obtain an improved background signal.

SUMMARY

In some aspects, the present disclosure provides compounds of the formula:

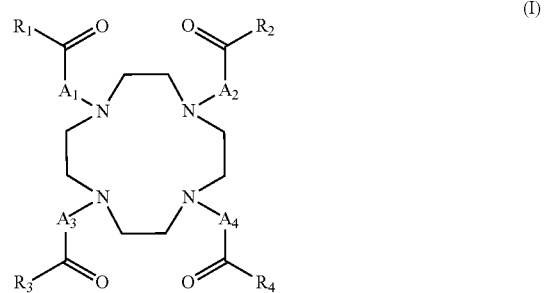

wherein:

$A_1$, $A_2$, $A_3$, and $A_4$ are each independently C1-C4 alkanediyl or substituted C1-C4 alkanediyl; and $R_2$, $R_3$, and $R_4$ are each independently hydroxy, amino, C1-C12 alkylamino, substituted C1-C12 alkylamino, C1-C12 dialkylamino, or substituted C1-C12 dialkylamino;

$R_1$ is

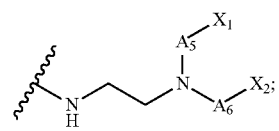

wherein:

$A_5$ and $A_6$ are each independently C1-C4 alkanediyl or substituted C1-C4 alkanediyl; and $X_1$ and $X_2$ are each independently C1-C12 heteroaryl or substituted C1-C12 heteroaryl;

provided that at least one of $A_1$, $A_2$, $A_3$, $A_4$, $A_5$, and $A_6$ is not —$CH_2$—;

or a metal complex, a deprotonated form, or a salt thereof. In some embodiments, the compounds are further defined as:

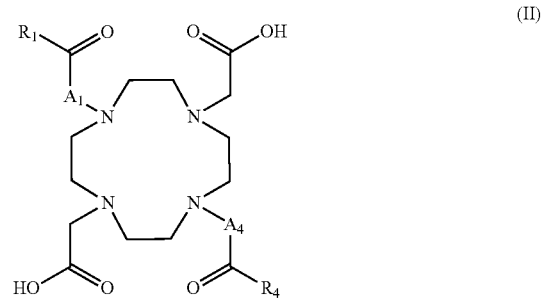

wherein:

$A_1$ and $A_4$ are each independently C1-C4 alkanediyl or substituted C1-C4 alkanediyl; and $R_4$ is hydroxy, amino, C1-C12 alkylamino, substituted C1-C12 alkylamino, C1-C12 dialkylamino, or substituted C1-C12 dialkylamino;

$R_1$ is

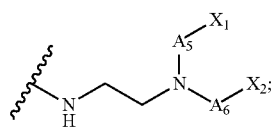

wherein:
As and $A_6$ are each independently C1-C4 alkanediyl or substituted C1-C4 alkanediyl; and
$X_1$ and $X_2$ are each independently C1-C12 heteroaryl or substituted C1-C12 heteroaryl;
provided that at least one of $A_1$, $A_4$, $A_5$, and $A_6$ is not —CH$_2$—;
or a metal complex, a deprotonated form, or a salt thereof.
In some embodiments, the compounds are further defined as:

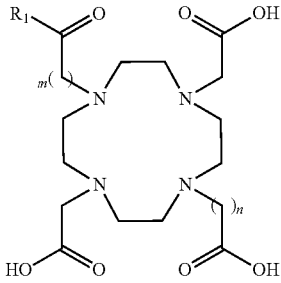

(III)

wherein:
m and n are each independently 1 or 2; and
$R_1$ is

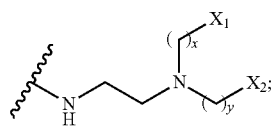

wherein:
x and y is 1 or 2; and
$X_1$ and $X_2$ are each independently C1-C12 heteroaryl or substituted C1-C12 heteroaryl;
provided that at least one of m, n, x, and y is not 1;
or a metal complex, a deprotonated form, or a salt thereof.

In some embodiments, $A_1$ is C1-C3 alkanediyl such as —CH$_2$— or —CH$_2$CH$_2$—. In some embodiments, $A_2$ is C1-C3 alkanediyl such as —CH$_2$—. In some embodiments, $A_3$ is C1-C3 alkanediyl such as —CH$_2$—. In some embodiments, $A_4$ is C1-C3 alkanediyl such as —CH$_2$— or —CH$_2$CH$_2$—. In some embodiments, As is C1-C3 alkanediyl such as —CH$_2$— or —CH$_2$CH$_2$—. In some embodiments, $A_6$ is C1-C3 alkanediyl such as —CH$_2$— or —CH$_2$CH$_2$—. In some embodiments, $R_4$ is hydroxy. In some embodiments, $R_2$ is hydroxy. In some embodiments, $R_3$ is hydroxy.

In some embodiments, $X_1$ is C1-C12 heteroaryl such as C1-C8 heteroaryl. In some embodiments, $X_1$ is pyridinyl such as 2-pyridinyl. In some embodiments, $X_2$ is C1-C12 heteroaryl such as C1-C8 heteroaryl. In some embodiments, $X_2$ is pyridinyl such as 2-pyridinyl. In some embodiments, m is 2. In some embodiments, n is 2. In some embodiments, x is 2. In some embodiments, y is 2.

In some embodiments, the compounds are further defined as:

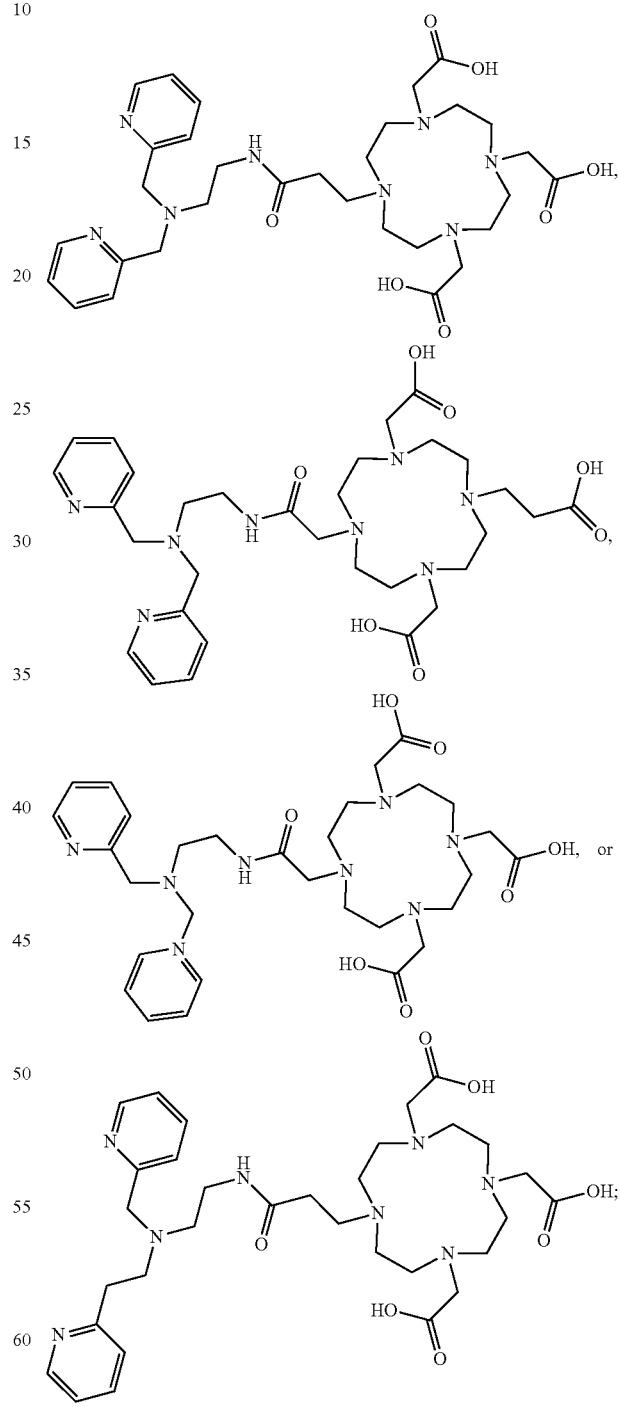

or a deprotonated form or salt thereof. In some embodiments, the compounds are further defined as a metal complex of the formula:

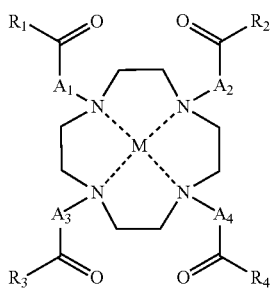

(I)

wherein:

$A_1$, $A_2$, $A_3$, and $A_4$ are each independently C1-C8 alkanediyl or substituted C1-C8 alkanediyl; and $R_2$, $R_3$, and $R_4$ are each independently hydroxy, amino, C1-C12 alkylamino, substituted C1-C12 alkylamino, C1-C12 dialkylamino, or substituted C1-C12 dialkylamino;

$R_1$ is

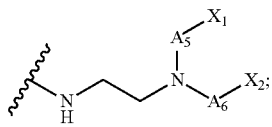

wherein:

$A_5$ and $A_6$ are each independently C1-C8 alkanediyl or substituted C1-C8 alkanediyl; and $X_1$ and $X_2$ are each independently C1-C12 heteroaryl or substituted C1-C12 heteroaryl;

provided that at least one of $A_1$, $A_2$, $A_3$, $A_4$, $A_5$, and $A_6$ is not —CH$_2$—;

or a deprotonated form or a salt thereof. In some embodiments, the metal complexes are further defined by the formula:

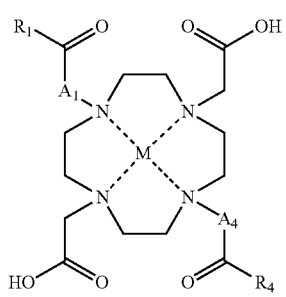

(V)

wherein:

$A_1$ and $A_4$ are each independently C1-C8 alkanediyl or substituted C1-C8 alkanediyl; and $R_4$ is hydroxy, amino, C1-C12 alkylamino, substituted C1-C12 alkylamino, C1-C12 dialkylamino, or substituted C1-C12 dialkylamino;

$R_1$ is

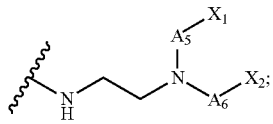

wherein:

$A_5$ and $A_6$ are each independently C1-C8 alkanediyl or substituted C1-C8 alkanediyl; and $X_1$ and $X_2$ are each independently C1-C12 heteroaryl or substituted C1-C12 heteroaryl;

provided that at least one of $A_1$, $A_4$, $A_5$, and $A_6$ is not —CH$_2$—;

or a deprotonated form or a salt thereof. In some embodiments, the metal complexes are further defined by the formula:

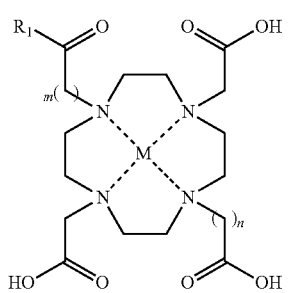

(VI)

wherein:

m and n are each independently 1, 2, 3, or 4; and $R_1$ is

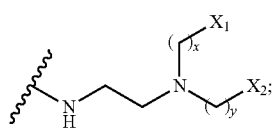

wherein:

x and y is 1, 2, 3, or 4; and $X_1$ and $X_2$ are each independently C1-C12 heteroaryl or substituted C1-C12 heteroaryl;

provided that at least one of m, n, x, and y is 1;

or a deprotonated form, or a salt thereof.

In some embodiments, M is a gadolinium ion such as Gd(III). In some embodiments, the compounds are further defined as:

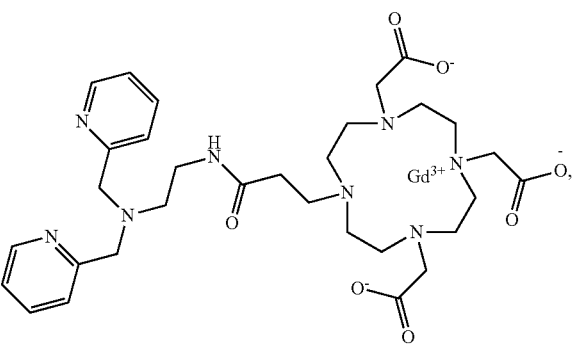

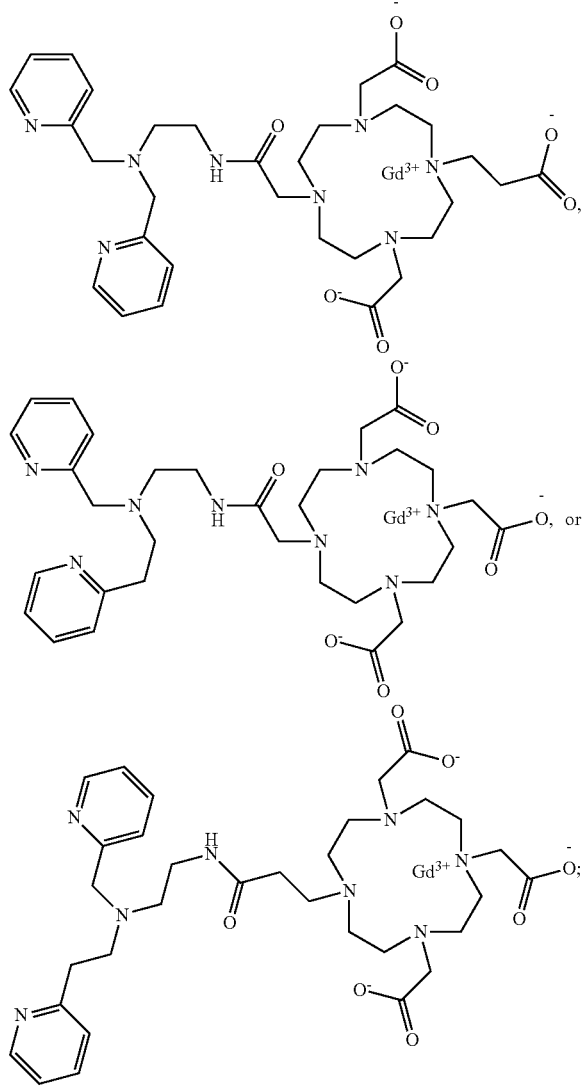

or a deprotonated form or salt thereof.

In still yet another aspect, the present disclosure provides pharmaceutical compositions comprising:
(A) a compound described herein; and
(B) an excipient.

In some embodiments, the pharmaceutical compositions are formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical compositions are formulated as a unit dose form in an amount sufficient to image a patient when administered thereto.

In yet another aspect, the present disclosure provides methods of imaging a patient comprising the steps of:
(A) administering to the patient a compound or composition described herein; and
(B) obtaining an imaging scan of the patient.

In some embodiments, the methods comprise detecting the presence of $Zn^{2+}$ ions in tissue.

In some embodiments, the collected imaging scan is from an MRI. In some embodiments, the methods further comprise analyzing the imaging scan. In some embodiments, analyzing the imaging scan comprises identifying changes in $Zn^{2+}$ concentration. In some embodiments, the imaging is performed in vivo. In some embodiments, analyzing the imaging scan produces a diagnosis of a disease such as diabetes mellitus or cancer. In some embodiments, the cancer is prostate cancer. In some embodiments, the patient is a mammal such as a human.

In still yet another aspect, the present disclosure provides methods of imaging the pancreas in vivo in a patient to determine the onset of β-cell degeneration comprising the steps of:
(A) administering to the patient a compound or composition described herein;
(B) obtaining an imaging scan of the patient; and
(C) determining the presence of $Zn^{2+}$ ions.

In some embodiments, the imaging scan is from an MRI. In some embodiments, the methods further comprise determining the concentration of $Zn^{2+}$ ions. In some embodiments, the methods further comprise administering insulin to the patient before collecting the imaging scan. In some embodiments, the onset of β-cell degeneration indicates the onset of diabetes mellitus. In some embodiments, the patient is a human.

In yet another aspect, the present disclosure provides methods of imaging the prostate in vivo in a patient to determine the presence of a prostate tumor comprising the steps of:
(A) administering to the patient a compound or composition described herein;
(B) obtaining an imaging scan of the patient; and
(C) determining the presence of $Zn^{2+}$ ions.

In some embodiments, the imaging scan is from an MRI. In some embodiments, the methods further comprise determining the concentration of $Zn^{2+}$ ions. In some embodiments, lower concentration of $Zn^{2+}$ ions indicates the presence of a prostate tumor such as a malignant prostate tumor. In some embodiments, the patient is a human.

In still yet another aspect, the present disclosure provides methods of imaging the pancreas in vivo in a patient to determine the secretion of insulin comprising the steps of:
(A) administering to the patient a compound or composition described herein;
(B) obtaining an imaging scan of the patient; and
(C) determining the presence of $Zn^{2+}$ ions.

In some embodiments, the imaging scan is from an MRI. In some embodiments, the methods further comprise determining the concentration of $Zn^{2+}$ ions. In some embodiments, the method comprises determining the secretion of insulin in an early phase insulin secretion. In other embodiments, the methods comprise determining the secretion of insulin in a late phase insulin secretion. In some embodiments, the patient is a human.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 7B) Enhancement profiles measured from pancreas ROI normalized to an external phantom show the distinct bi-phasic profile only for GdL4 (FIG. 7C) Area under the curve (AUC) for each sensor and control Gd-HPDO3A for t=11–19 minutes post-glucose stimulation. GdL4, weak binding affinity to $Zn^{2+}$, shows improved bi-phasic profile compared to control and to stronger affinity agents such as GdL1 (* p<0.05, ** p<0.01). *GdDO2A-diBPEN derivative shown in Supplementary Information as GdDO2A-diBPEN-propylamide.

DESCRIPTION OF ILLUSTRATIVE EMBODIMENTS

Figure 1:
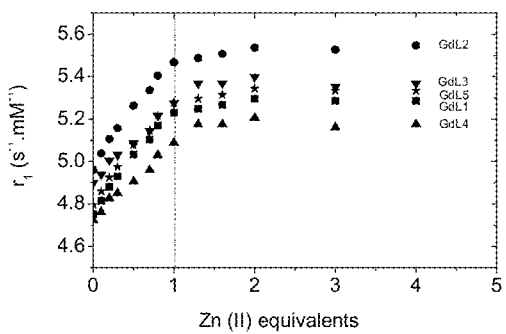
FIG. 1 shows the plot of $r_1$ relaxivity of GdL1-5 at 0.5T and 37° C. upon addition of $ZnCl_2$ (no HSA). All solutions were prepared in 100 mM Tris buffer at pH 7.4.
Figure 2A:
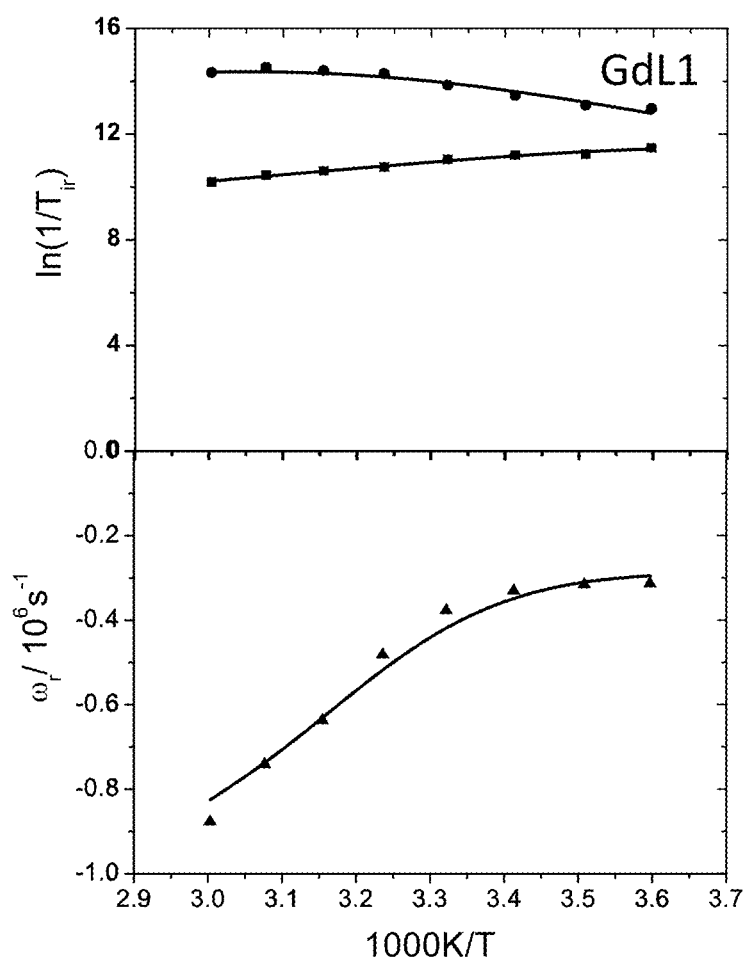
FIGS. 2A-2E show the temperature dependence of the reduced longitudinal (■) and transverse (▲) $^{17}O$ relaxation rates and reduced chemical shifts (•) of the Gd-complexes (GdL1, FIG. 2A, GdL2, FIG. 2B, GdL3, FIG. 2C, GdL4, FIG. 2D, GdL5, FIG. 2E) in aqueous solution ($B_0$=9.4 T, $[Gd^{3+}]$=25 mM). The solid line represents the least-square fitting of the experimental data.
Figure 2B:
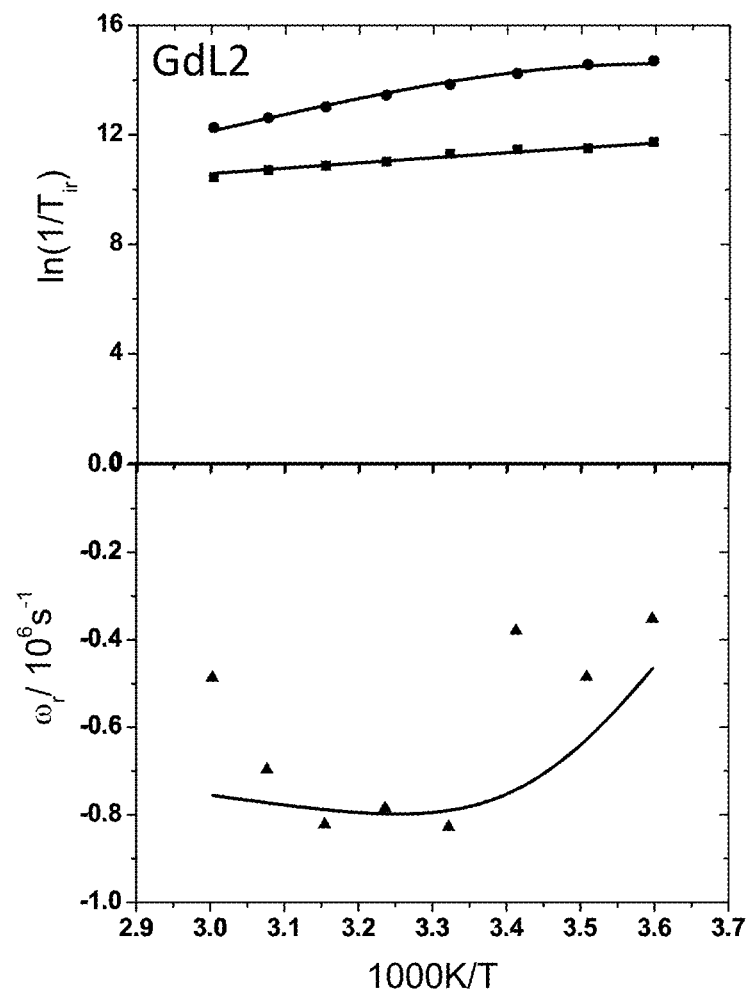
Figure 2C:
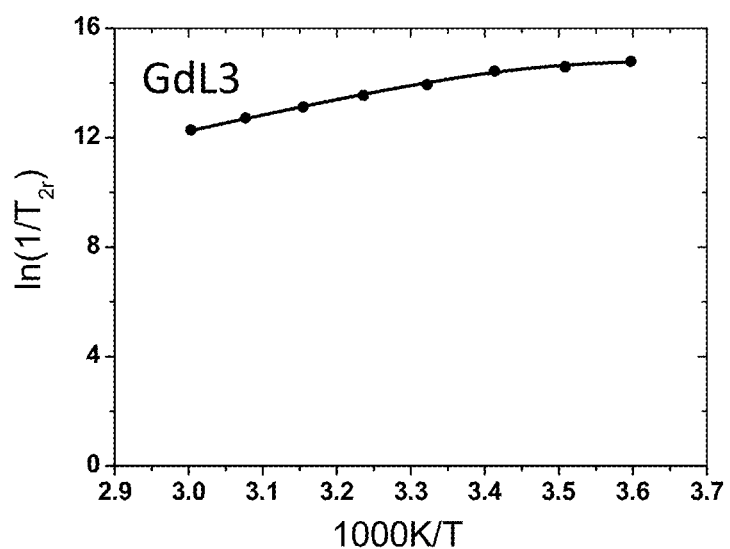
Figure 2D:
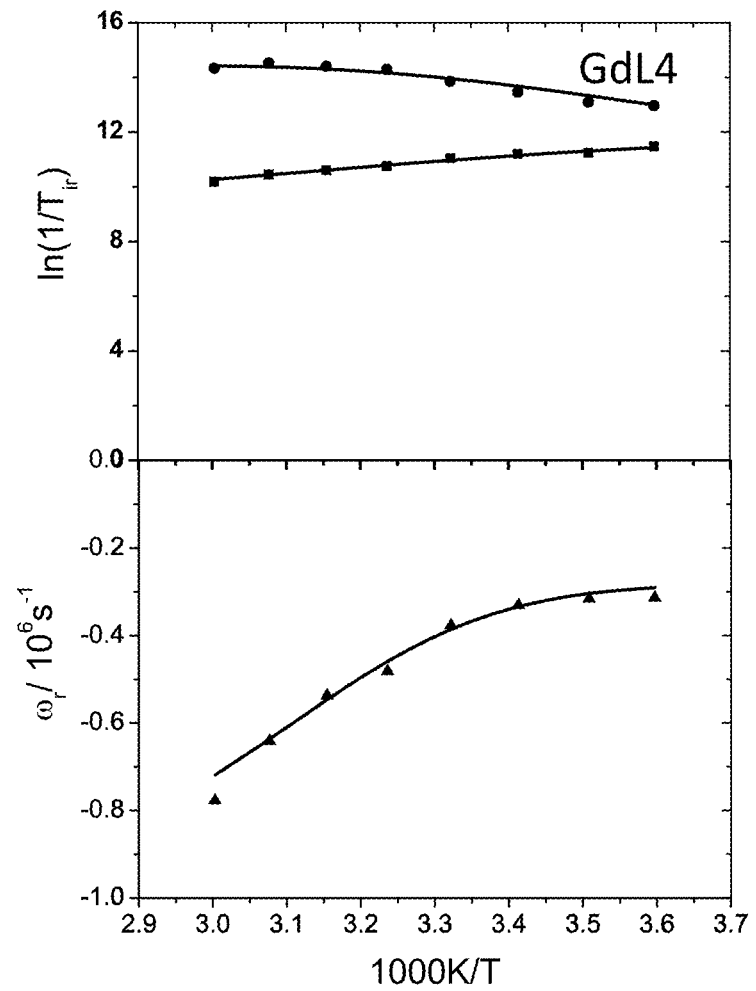
Figure 2E:
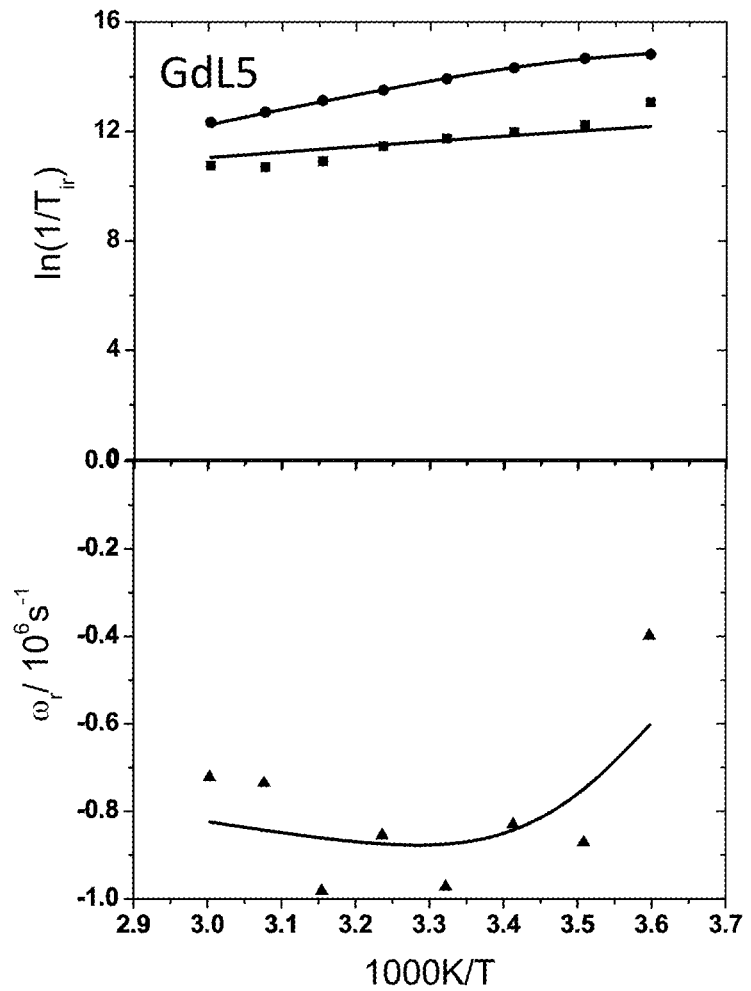

In some aspects, the present disclosure provides contrast agents containing a central gadolinium(III) 1,4,7,10-tetraazacyclododecane-1,4,7,10-tetraacetic acid (DOTA) moiety and a single zinc binding group attached to that central core through a linker. These particular compounds may show an improved water exchange rate while maintaining zinc binding. Additionally, the compounds described herein may have weaker zinc binding to prevent saturation of the zinc signaling and improve the relative background signal compared to compounds with higher zinc binding.

A. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means=NH; "cyano" means —CN; "isocyanate" means —N=C=O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double or may represent a dative or coordination bond to a metal atom. The symbol "====" represents a single bond or a double bond. Thus, for example, the formula

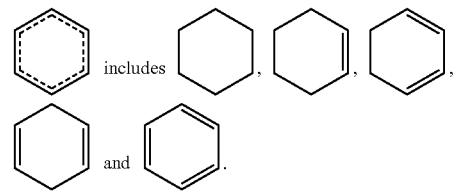

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol " ~~~ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "⁓" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M—C, M=C, M----C, and M⏃C, each refers to a bond of any and type and order between a metal atom and a carbon atom. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

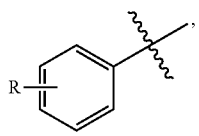

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH₃ (Me), —CH₂CH₃ (Et), —CH₂CH₂CH₃ (n-Pr or propyl), —CH(CH₃)₂ (i-Pr, ⁱPr or isopropyl), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or tBu), —CH₂C(CH₃)₃ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂— (methylene),

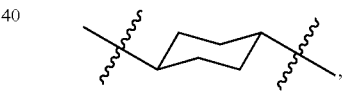

—CH₂CH₂—, —CH₂C(CH₃)₂CH₂—, —CH₂CH₂CH₂—, and are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH₂, =CH(CH₂CH₃), and =C(CH₃)₂. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

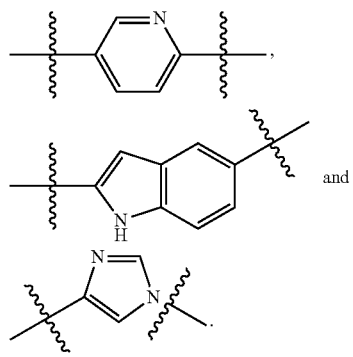

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaralkyl" when used without the "substituted" modifier refers to the monovalent group —alkanediyl—heteroaryl, in which the terms alkanediyl and aryl are each used in a manner consistent with the definitions provided above. Non-limiting examples of heteroaralkyls are: 2-pyridinylmethyl and 2-imidazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(0)$_2$NH$_2$. Non-limiting examples of substituted heteroaralkyls are: (3-hydroxypyridinyl)-methyl, and 3-chloro-2-thiazolylethyl.

The term "metal complex" is a compound comprising at least one compound which can act as a ligand (i.e. contains at least one pair of electrons, a charge, or an empty orbital) and at least one metal ion, wherein the ligand and the metal ion are attached to one another by one or more metal-ligand bonds.

The term "deprotonated form" is a compound in which one or more acidic hydrogen atoms have been removed to from an anion. In some embodiments, an acidic hydrogen has a pK$_a$ less than 20. In a preferred embodiments, the pK$_a$ is less than 10. In a more preferred embodiment, the pK$_a$ is less than 7.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. COMPOUNDS

In some aspects, the present disclosure provides novel ligands of the formula:

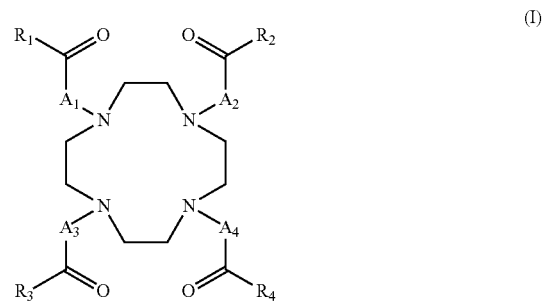

(I)

wherein:
$A_1$, $A_2$, $A_3$, and $A_4$ are each independently C1-C4 alkanediyl or substituted C1-C4 alkanediyl; and
$R_2$, $R_3$, and $R_4$ are each independently hydroxy, amino, C1-C12 alkylamino, substituted C1-C12 alkylamino, C1-C12 dialkylamino, or substituted C1-C12 dialkylamino;
$R_1$ is

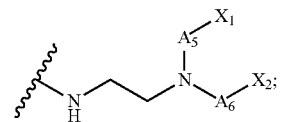

wherein:
$A_5$ and $A_6$ are each independently C1-C4 alkanediyl or substituted C1-C4 alkanediyl; and
$X_1$ and $X_2$ are each independently C1-C12 heteroaryl or substituted C1-C12 heteroaryl;
provided that at least one of $A_1$, $A_2$, $A_3$, $A_4$, $A_5$, and $A_6$ is not —$CH_2$—;
or a metal complex, a deprotonated form, or a salt thereof.

In some embodiments, the compounds of the present disclosure are included in Table 1. These compounds may also be referred to as complexes throughout the application.

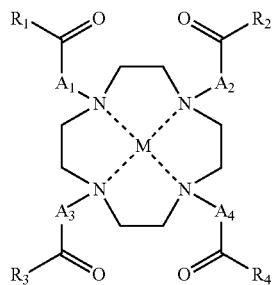

wherein:

$A_1$, $A_2$, $A_3$, and $A_4$ are each independently C1-C8 alkanediyl or substituted C1-C8 alkanediyl; and $R_2$, $R_3$, and $R_4$ are each independently hydroxy, amino, C1-C12 alkylamino, substituted C1-C12 alkylamino, C1-C12 dialkylamino, or substituted C1-C12 dialkylamino;

$R_1$ is

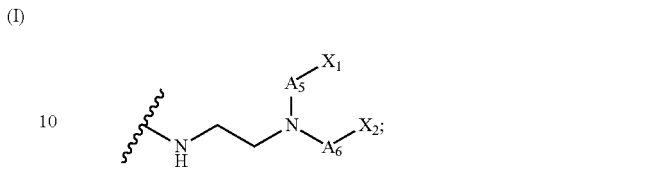

wherein:

$A_5$ and $A_6$ are each independently C1-C8 alkanediyl or substituted C1-C8 alkanediyl; and $X_1$ and $X_2$ are each independently C1-C12 heteroaryl or substituted C1-C12 heteroaryl;

provided that at least one of $A_1$, $A_2$, $A_3$, $A_4$, $A_5$, and $A_6$ is not —CH$_2$—;

or a deprotonated form or a salt thereof.

TABLE 1

| Compounds of the Present Disclosure | |
| --- | --- |
| Compound Number | Compound |
| GdL1 | 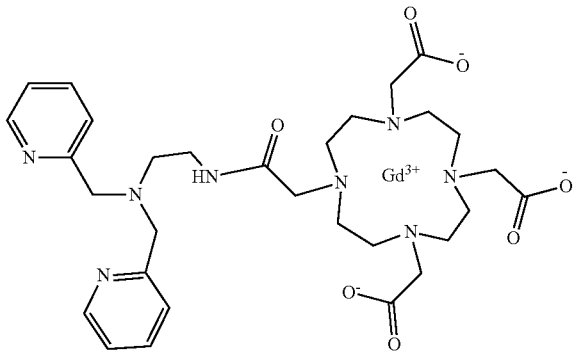 |
| GdL2 | 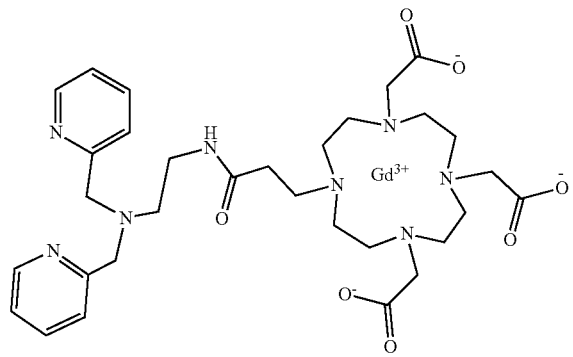 |

TABLE 1-continued

Compounds of the Present Disclosure

| Compound Number | Compound |
|---|---|
| GdL3 | 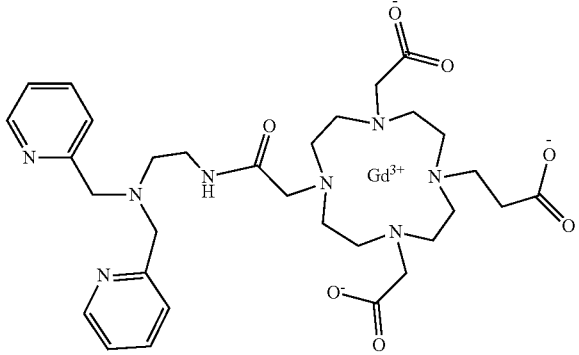 |
| GdL4 | 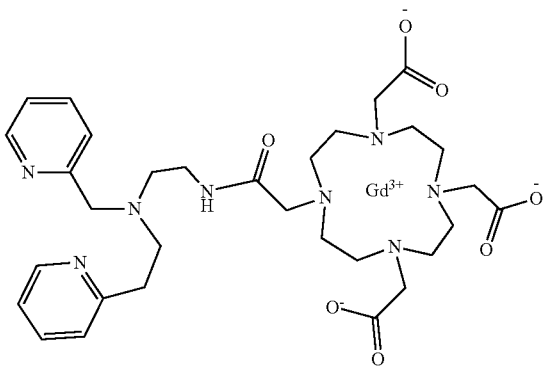 |
| GdL5 | 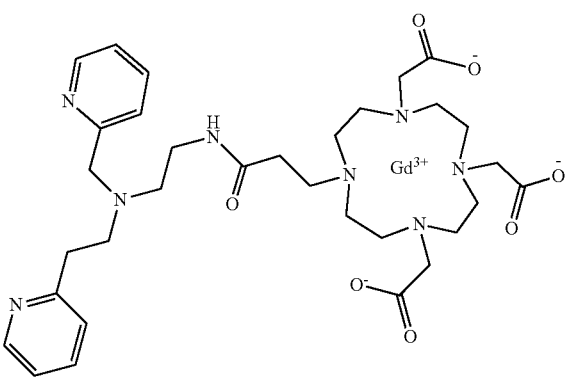 |

The novel compounds, complexes, and ligands provided herein, may be prepared according to the methods described below. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

The ligands described in this disclosure may contain one or more asymmetrically-substituted carbon or nitrogen atoms, and may be isolated in optically active or racemic form. Thus, all chiral, diastereomeric, racemic, epimeric, and all geometric isomeric forms of a structure are intended, unless the specific stereochemistry or isomeric form is specifically indicated. The ligands of this disclosure may occur as racemates and racemic mixtures, single enantiomers, diastereomeric mixtures and individual diastereomers. In some embodiments, a single diastereomer is obtained. The chiral centers of the present disclosure can have the S or the R configuration.

In addition, atoms making up the ligands of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of the ligands may be replaced by a sulfur or selenium atom(s).

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in Handbook of Pharmaceutical Salts: Properties, and Use (2002), which is incorporated herein by reference.

In some embodiments, compounds of the disclosure also have the advantage that they are more efficacious than, less toxic than, longer acting than, more potent than, produce fewer side effects than, more easily absorbed than, and/or have a better pharmacokinetic profile (e.g., higher oral bioavailability and/or lower clearance) than, and/or have other useful pharmacological, physical, or chemical properties over, known compounds, whether for use in the indications stated herein or otherwise.

C. PREPARATION OF LIGAND AND IMAGING CHARACTERIZATION

1. Synthesis

In some embodiments, the present ligand can be prepared by selectively protected the amine groups of the DOTA to allow for the introduction of a unique group to each of the linkers. In some embodiments, this modification is carried out using orthogonally protected bifunctional linkers containing a carboxylate group and a leaving group such as a halogen. In some embodiments, this reaction is carried out using a standard nucleophilic displacement. The orthogonally protected carboxylate can then be deprotected and coupled to additional functional groups though standard amide bond forming methodologies.

Furthermore, the complex can be metalated before, during, or after the synthesis of the functional groups on the amines of the DOTA macrocycle provided that the synthetic methods are not negatively affect by the presence of the metal ion. In some embodiments, the metal ion is introduced into the DOTA compound after the introduction of the functional groups to the amines of the DOTA macrocycle.

2. Relaxometric Studies

In some embodiments, MRI contrast agents are typically characterized by a $T_1$ proton relaxivity value. The relaxivity of a low molecular weight Gd-ligand complex that has rapid water exchange kinetics may be dominated by the inner-sphere contribution. Without being bound by theory, the Solomon—Bloembergen—Morgan (SBM) theory of relaxivity predicts that inner-sphere contribution to relaxivity may be dependent on several parameters including the number of inner-sphere water molecules (q), the longitudinal relaxation time of the protons of the water molecule(s) in the inner coordination sphere, the residence time of the inner-sphere water molecule(s) and the tumbling rate of the paramagnetic complex in solution (rotational correlation time) (Caravan, et al., 1999).

3. MRI Imaging and Relaxivity Measurements

The efficacy of the probe is measured by the longitudinal relaxation rate of the water protons, which is known as relaxivity ($r_1$) (Shiraishi, et al., 2010; Huang, et al., 2011) or the measurement of other physical parameters. Without being bound by theory, according to the Bloembergen-Solomon-Morgan theory, in some embodiments, the residence lifetime of the coordinated water molecules and the rotational correlation times are factors for enhancing the relaxivities of gadolinium complexes, which are related to the intrinsic structural parameters. In some embodiments, the relaxation theory also predicts that higher relaxation rates can be obtained upon increase of the rotational correlation time of complexes. In some embodiments, small, fast tumbling molecules like Gd-DTPA show a modest decrease in $r_1$ with increasing field strength (Rohrer, et al., 2005), while big molecular weight contrast agent have high relaxivities that peak between 0.5 and 1.0 T and then sharply drop with increasing field (Rohrer, et al., 2005; Caravan, 2006).

D. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Synthetic Scheme and Experimental Procedures

Scheme 1 Chemical structures of GdDO3A-monoBPEN or monoPEPMA derivatives (GdL1-5).

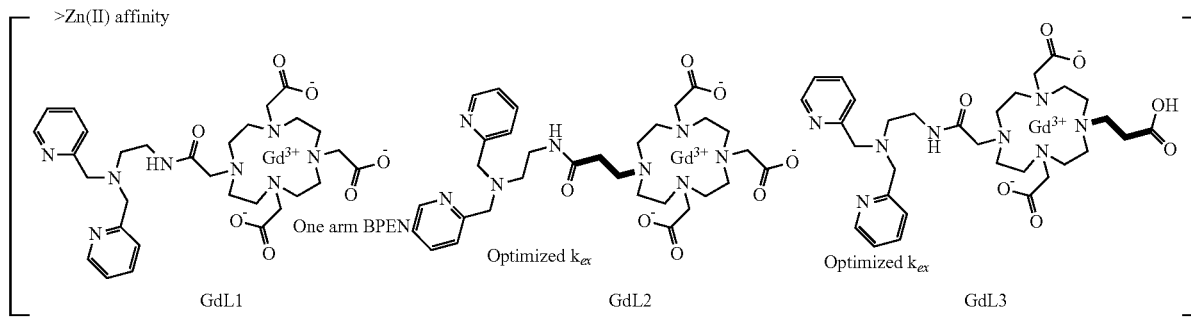

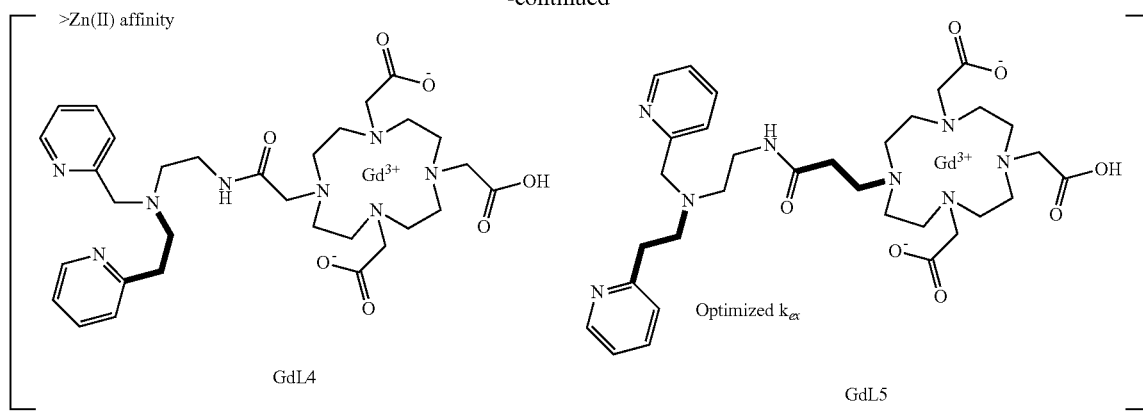

GdL4

GdL5 (Optimized $k_{ex}$)

The structures of the five agents reported here, GdL1-5, are shown in Scheme 1. The full synthetic details of their preparation are described below. An extra methylene carbon was included in either an acetate (GdL3) or acetamide (GdL2 and GdL5) side-chain to increase steric hindrance around the $Gd^{3+}$-water coordination site and thereby increase $k_{ex}$ (Yu et al., 2015; Jaszberenyi et al., 2005) The strategy used to alter the binding affinity for zinc was similar. In this case, a modified version of the BPEN structure, [2-(pyridin-2-yl)ethyl] (pyridin-2-yl methyl)amine or PEPMA, a ligand known to have a lower affinity for $Zn^{2+}$, was used to prepare GdL4 and GdL5 (De Leon-Rodriguez et al., 2012). In general, the synthetic pathway to each agent involved coupling a $Zn^{2+}$-binding moiety (B PEN or PEPMA) via either alkylation or amide coupling to tris-t-butyl-DO3A. After hydrolysis and purification by HPLC, the $Gd^{3+}$ complexes were prepared, and these were subsequently purified and characterized using standard methods (preparative HPLC, 1H NMR, 13C NMR, and MS).

All reagents and solvents were purchased from commercial sources and used as received unless otherwise noted. Human serum albumin (HSA, fatty acid and globulin free) was purchased from Sigma-Aldrich. Silica gel (200-400 mesh, 60A) for column chromatography was purchased from Sigma-Aldrich. TLC analyses were conducted using EMD Millipore precoated aluminum oxide or Whatman precoated silica gel on polyester plates. Lanthanide chloride stock solutions (0.035 M of $GdCl_3$ and 0.576 M of $EuCl_3$) were standardized with EDTA standard solution (0.005 M) using xylenol orange as the endpoint indicator in acetate buffer (pH=5.8). All hydrogenation reactions were carried out using a Parr hydrogenation apparatus. 1H and 13C NMR spectra of all synthetic intermediates, final products, $^{17}O$ temperature studies of all lanthanide complexes were recorded on a Bruker AVANCE III 400 MHz NMR spectrometer. Analytical HPLC was performed on an Agilent Technologies 1220 Infinity LC using a RESTEK Ultra C-18 IBD column (3 μm, 100×4.6 mm). Preparative HPLC was performed on a Waters Delta Prep HPLC system equipped with a Water® 2996 photodiode array detector and a Phenomenex Kinetex® C18 column (5 μm, 21.2 mm×250 mm) or an Atlantis Prep T3 OBD Column (5 μm, 30 mm×250 mm). A Fisher Science Education pH-meter coupled with Thermo Scientific Orion Micro pH electrode was used for pH measurements. Milli-Q purified water was used for the preparation of all samples and for preparative and analytical HPLC. A VirTis Freeze Dryer (Benchtop-k) was used to lyophilize the samples. Mass spectra were obtained using either a HT Laboratories (San Diego, Calif.) instrument or a Waters Alliance e2695 Separations Module coupled with Xevo QT of MS using an Atlantis T3 Column (5 μm, 6 mm×250 mm) at The Advanced Imaging Research Center (University of Texas Southwestern Medical Center, Dallas). The metal concentrations were determined via Inductively Coupled Plasma (ICP) from UTD. Chemical structures and IUPAC names were obtained using Chemaxon MarvinSketch 6.2.0.

Scheme 2. Synthetic pathway for the DO3A-BPHEN/PEPMA (L1-5) derivatives.

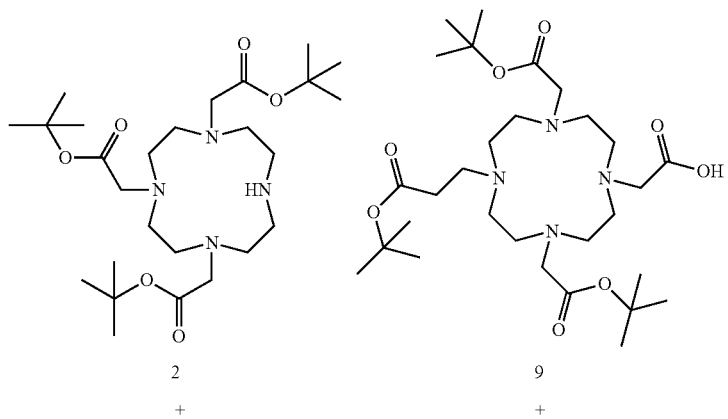

2 +    9 +

-continued
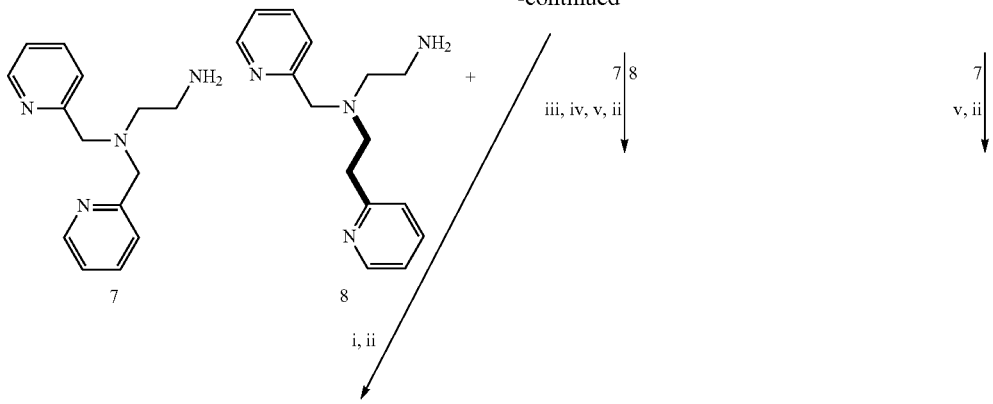
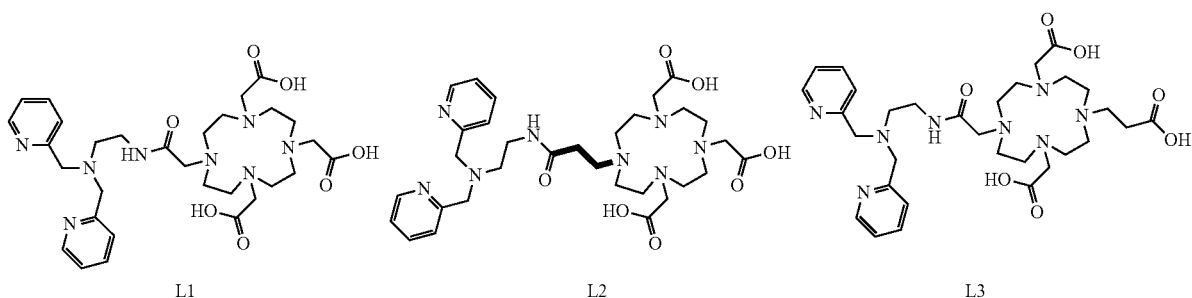
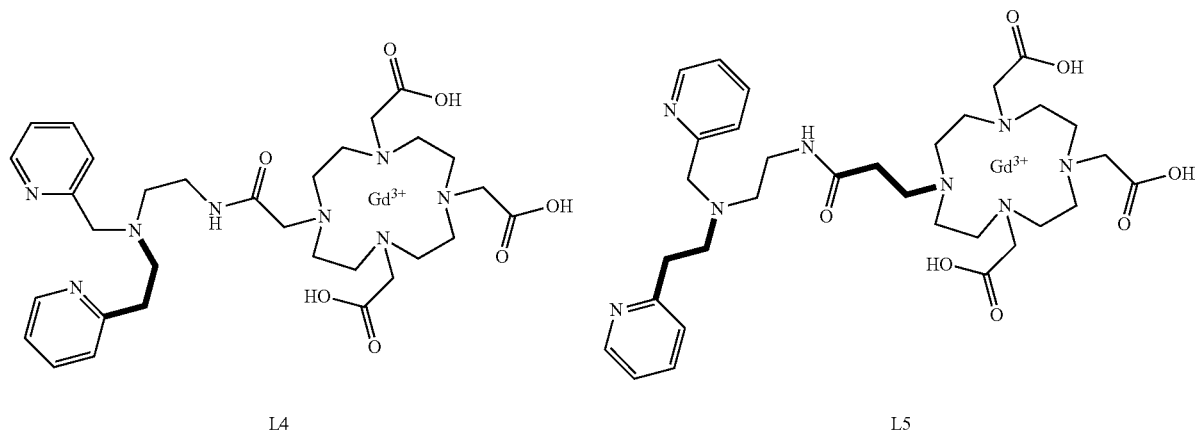
Scheme 3: Synthesis of L1: i) K$_2$CO$_3$, CH$_3$CN, reflux, 2 days, ii) TFA, RT, overnight (73%).
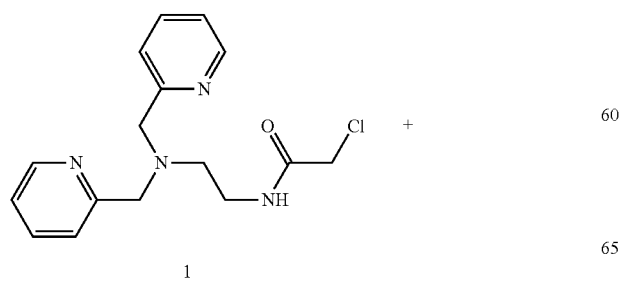

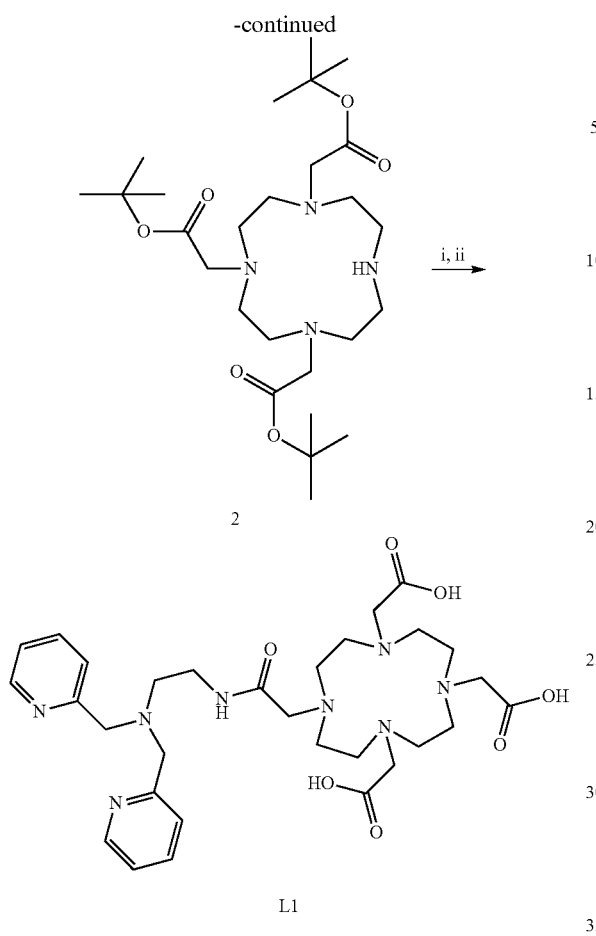

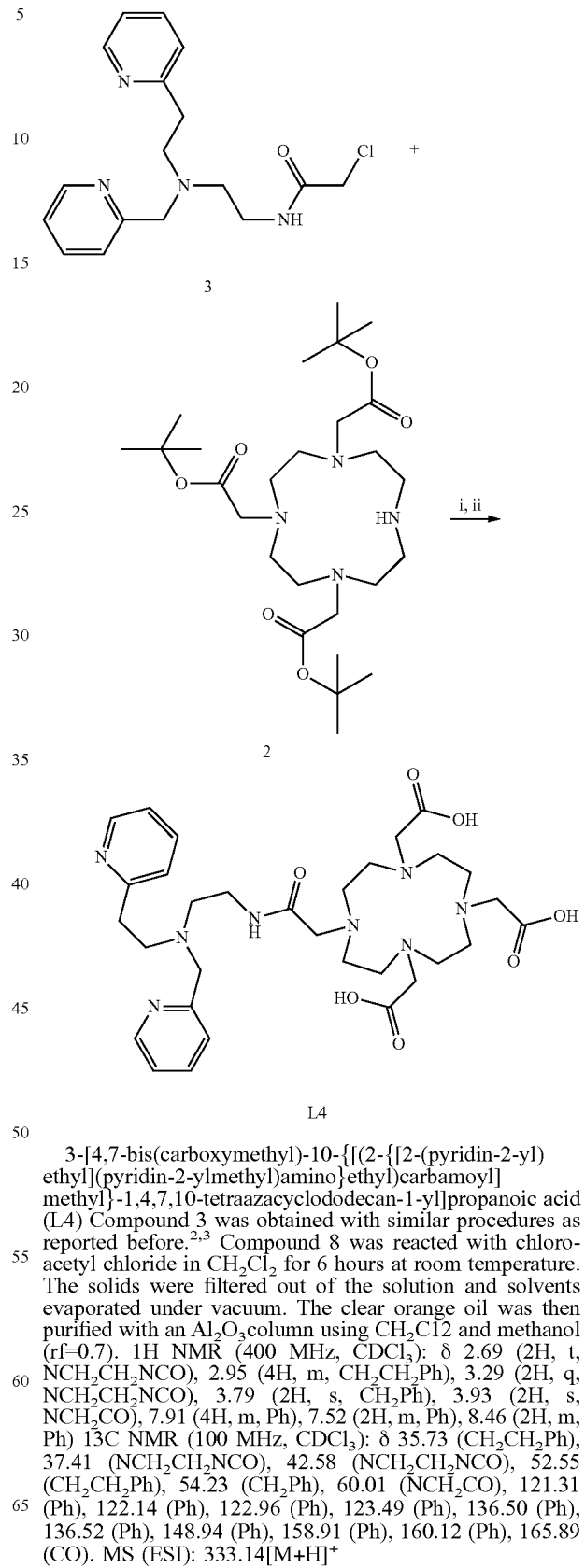

Scheme 4 Synthesis of L4: i) $K_2CO_3$, $CH_3CN$, reflux, 2 days, ii) TFA, RT, overnight (61%).

3-{4-[({2-[bis(pyridin-2-ylmethyl)amino]ethyl}carbamoyl)methyl]-7,10-bis(carboxymethyl)-1,4,7,10-tetraazacyclododecan-1-yl}propanoic acid (L1) Synthesis for compound 1 was reported before (Yu et al., 2015) Compound 1 (0.4 g, 0.72 mmol) was suspended in 100 mL $CH_3CN$. Compound 2 (0.35 g, 0.68 mmol) together with potassium carbonate (2.14 g, 15.50 mmol) were added. The volume was increased to 250 mL and the suspension was refluxed for 48 hours. The mixture was filtered, solvents were removed in vacuo, residue dissolved in dichloromethane and washed with an aqueous solution of NaOH (pH ~10). Organic phase was collected and dried with $MgSO_4$. The crude product was checked by 1H NMR and MS, and used in the next step without further purification, it was dissolved in 100 mL TFA and stirred overnight to afford L1. The solution was evaporated in vacuo and the resulting product was purified using preparative HPLC. The ligand was obtained as a white powder (0.32 g, 0.48 mmol, 73%). 1H NMR (400 MHz, D2O): δ 2.71 (2H, s, $NCH_2CH_2NCO$), 3.40 (24H, m, br, macrocycle $CH_2$, $NHCH_2CH_2NH$, $CH_2$, $NCH_2COOH$, $CH_2$, $NCH_2CONH$), 4.13 (2H, s, br, $NCH_2CH_2NCO$ and 4H, s, $CH_2Ph$), 7.86 (2H, dd, Ph), 7.98 (2H, d, Ph), 8.41 (2H, dd, Ph), 8.58 (2H, d, Ph). 13C NMR (100 MHz, D2O): δ 36.64 ($NCH_2CH_2NCO$), 51.84 (macrocycle $CH_2$), 51.94 (macrocycle $CH_2$), 52.67 (macrocycle $CH_2$), 52.89 (macrocycle $CH_2$), 52.89 ($NCH_2COOH$), 54.19 ($NCH_2CH_2NCO$), 54.28 ($NCH_2CO$), 55.05 ($CH_2Ph$), 126.32 (Ph), 126.34 (Ph), 141.80 (Ph), 147.24 (Ph), 152.40 (Ph), 168.33 (CO), 174.27 (COOH), 174.49 (COOH). MS (ESI): 628.89 $[M+H]^+$;

3-[4,7-bis(carboxymethyl)-10-{[(2-{[2-(pyridin-2-yl)ethyl](pyridin-2-ylmethyl)amino}ethyl)carbamoyl]methyl}-1,4,7,10-tetraazacyclododecan-1-yl]propanoic acid (L4) Compound 3 was obtained with similar procedures as reported before.[2,3] Compound 8 was reacted with chloroacetyl chloride in $CH_2Cl_2$ for 6 hours at room temperature. The solids were filtered out of the solution and solvents evaporated under vacuum. The clear orange oil was then purified with an $Al_2O_3$ column using $CH_2Cl_2$ and methanol (rf=0.7). 1H NMR (400 MHz, $CDCl_3$): δ 2.69 (2H, t, $NCH_2CH_2NCO$), 2.95 (4H, m, $CH_2CH_2Ph$), 3.29 (2H, q, $NCH_2CH_2NCO$), 3.79 (2H, s, $CH_2Ph$), 3.93 (2H, s, $NCH_2CO$), 7.91 (4H, m, Ph), 7.52 (2H, m, Ph), 8.46 (2H, m, Ph) 13C NMR (100 MHz, $CDCl_3$): δ 35.73 ($CH_2CH_2Ph$), 37.41 ($NCH_2CH_2NCO$), 42.58 ($NCH_2CH_2NCO$), 52.55 ($CH_2CH_2Ph$), 54.23 ($CH_2Ph$), 60.01 ($NCH_2CO$), 121.31 (Ph), 122.14 (Ph), 122.96 (Ph), 123.49 (Ph), 136.50 (Ph), 136.52 (Ph), 148.94 (Ph), 158.91 (Ph), 160.12 (Ph), 165.89 (CO). MS (ESI): 333.14 $[M+H]^+$ Compound L4 synthesis was performed as described above for L1. The ligand was obtained as a white powder (0.27 g, 0.41 mmol, 61%). 1H NMR (400 MHz, D20): δ 2.48 (2H, m, $CH_2CH_2Ph$), 2.78-3.25 (28H, br, macrocycle $CH_2$, $NCH_2CH_2NCO$ $NHCH_2CH_2N$, $NCH_2COOH$, $NCH_2CO$), 3.04 (2H, m, $CH_2CH_2Ph$), 3.86 (2H, s, $CH_2Ph$), 7.91 (4H, b, Ph), 8.43 (2H, m, Ph), 8.59 (2H, s, Ph). 13C NMR (100 MHz, D20): δ 36.61 ($CH_2CH_2Ph$), 41.86 ($NCH_2CH_2NCO$), 47.27 ($NCH_2CH_2NCO$), 48.88 ($CH_2CH_2Ph$), 51.74 (macrocycle $CH_2$), 52.40 (macrocycle $CH_2$), 52.64 (macrocycle $CH_2$), 53.55 (macrocycle $CH_2$) 54.91 ($NCH_2COOH$), 55.09 ($CH_2Ph$), 124.34(Ph), 126.32 (Ph), 141.80 (Ph), 147.24 (Ph), 152.10 (Ph), 168.33 (CO), 173.97(COOH). MS (ESI): 643.03$[M+H]^+$;

Scheme 5. Synthesis of 6. Reagents and conditions: (iii) benzyl acrylate 4, $CH_3CN$, 2 days (78%); (iv) $H_2$ (60 psi), Pd/C, EtOH, RT, 12 hours (95%).

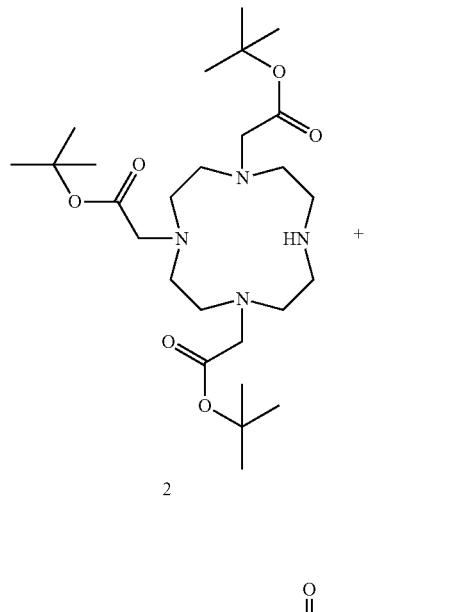

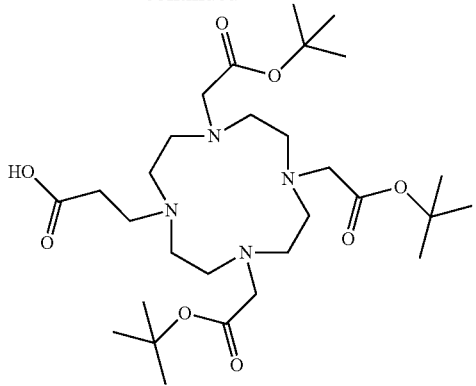

3-{4,7,10-tris[2-(tert-butoxy)-2-oxoethyl]-1,4,7,10-tetraazacyclododecan-1-yl}propanoic acid (6) To a solution of 2, 2.0 g, 3.90 mmol) in anhydrous $CH_3CN$ (100 mL) was added 1,8-diazabicyclo[5.4.0]undec-7-ene, DBU (0.30 g, 1.95 mmol, 0.5 eq) and benzyl acrylate 4 (9.45 g, 3.90 mmol) at room temperature. The reaction mixture was stirred at 50° C. under $N_2$ for 2 days. The solvent was removed in vacuo and water (500 ml) was added. The mixture was extracted with dichloromethane (3×200 ml) and the combined organic layer was dried over $MgSO_4$ and concentrated in vacuo to give 5 (2.06 g, 3.04 mmol, 78%) as crude product that was used for the next step without purification. To compound 5 dissolved in ethanol (150 mL) was added palladium on carbon (10%, 200 mg). The reaction mixture was shaken in a Parr high pressure hydrogenation apparatus and allowed to react at a hydrogen pressure of 60 psi at room temperature for 12 hours. The black reaction mixture was filtered through celite and the resulting colorless solution was then evaporated in vacuo to afford 6 as a colorless oil (1.69 g, 2.88 mmol, 95%). 1H NMR (400 MHz, $CDCl_3$): δ 1.29 (6H, t, $3J_{HH}$=7.2 Hz, $CH_3CH_2O$), 1.41 (9H, s, $C(CH_3)_3$), 1.47 (9H, s, $C(CH_3)_3$), 2.40-3.51 (26H, m, br, macrocycle $CH_2$ and side arm $CH_2$), 4.15 (4H, br, $CH_3CH_2O$). 13C NMR (100 MHz, $CDCl_3$): δ 14.16 ($CH_3CH_2O$), 27.98 ($C(CH_3)_3$), 31.12 ($NCH_2CH_2COOH$), 49.56 ($NCH_2CH_2COOH$), 51.88 (macrocycle $CH_2$), 55.98 (br, $NCH_2COOH$), 57.15 (br, $NCH_2CO_2$), 61.03 ($CH_3CH_2O$), 80.58 ($C(CH_3)_3$), 82.10 ($C(CH_3)_3$), 172.26 (C=O), 172.51 (C=O), 172.74 (C=O). MS (ESI): 587.35 $[M+H]^+$, 1173.60 $[2M+H]^+$.

Scheme 6. Synthesis of L2. Reagents and conditions: (v) HBTU, DMF, DIPEA, 12hours, ii) TFA, RT, overnight (64%).

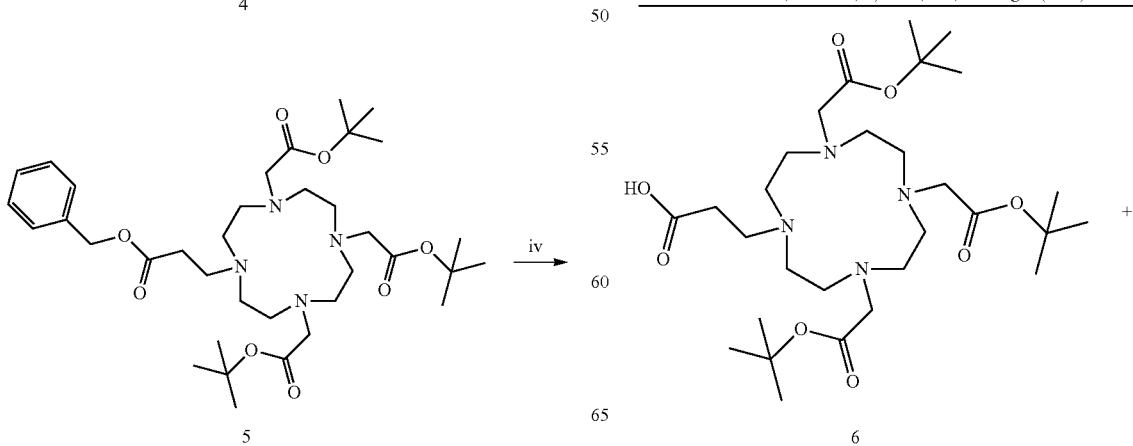

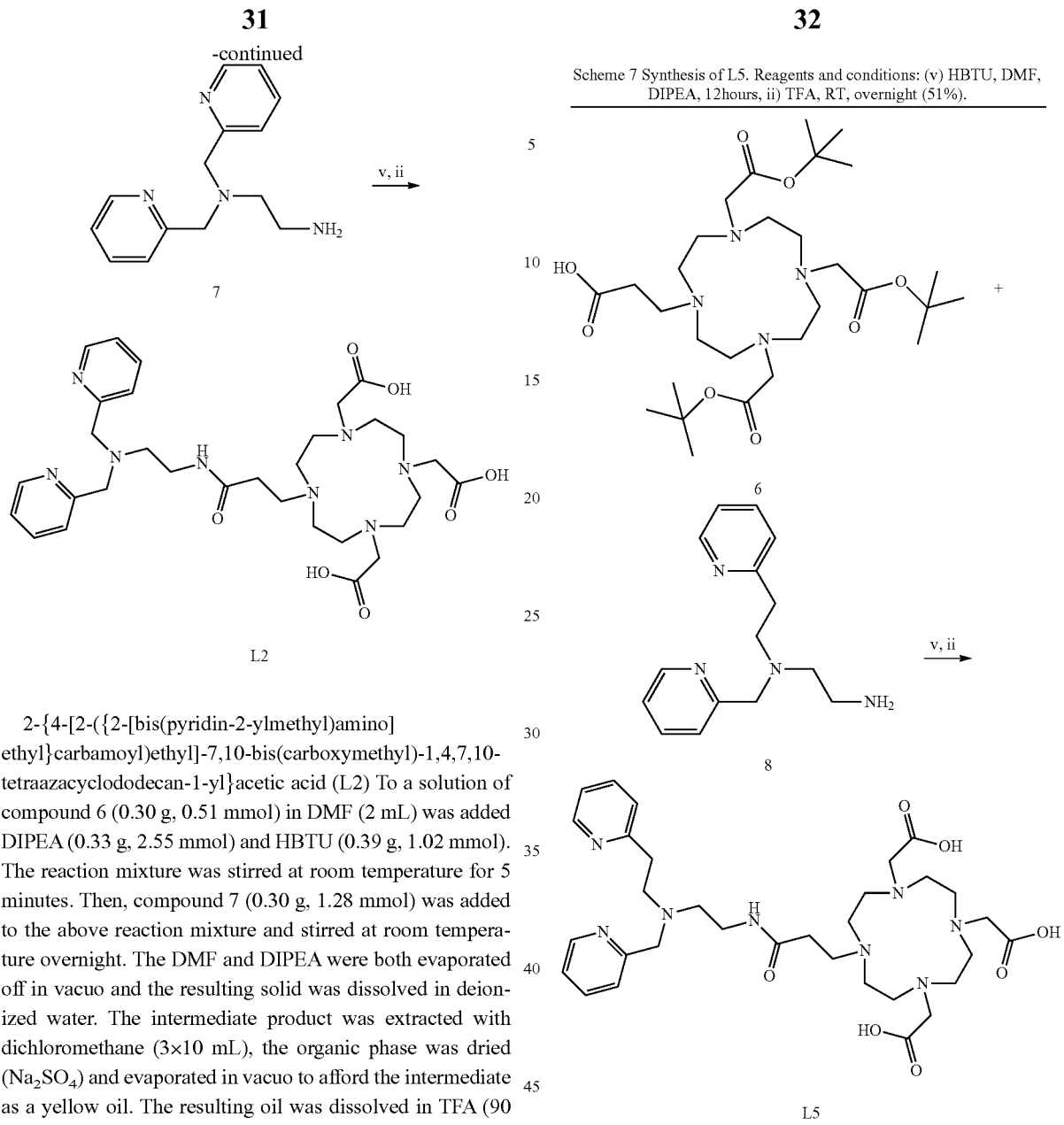

Scheme 7 Synthesis of L5. Reagents and conditions: (v) HBTU, DMF, DIPEA, 12hours, ii) TFA, RT, overnight (51%).

2-{4-[2-({2-[bis(pyridin-2-ylmethyl)amino]ethyl}carbamoyl)ethyl]-7,10-bis(carboxymethyl)-1,4,7,10-tetraazacyclododecan-1-yl}acetic acid (L2) To a solution of compound 6 (0.30 g, 0.51 mmol) in DMF (2 mL) was added DIPEA (0.33 g, 2.55 mmol) and HBTU (0.39 g, 1.02 mmol). The reaction mixture was stirred at room temperature for 5 minutes. Then, compound 7 (0.30 g, 1.28 mmol) was added to the above reaction mixture and stirred at room temperature overnight. The DMF and DIPEA were both evaporated off in vacuo and the resulting solid was dissolved in deionized water. The intermediate product was extracted with dichloromethane (3×10 mL), the organic phase was dried ($Na_2SO_4$) and evaporated in vacuo to afford the intermediate as a yellow oil. The resulting oil was dissolved in TFA (90 mL) and stirred overnight. The solution was evaporated to give the crude product that was then purified using preparative HPLC to afford the pure ligand as a white powder (210 mg, 0.33 mmol, 64%, two steps). 1H NMR (400 MHz, D20): δ 2.54 (4H, m, $CH_2CH_2CO$ and $NCH_2CH_2NCO$), 2.75-3.34 (16H, br, macrocycle $CH_2$), 2.80 (2H, m, $CH_2CH_2CO$), 3.34 (6H, br, $CH_2COOH$), 3.90 (2H, m, $NCH_2CH_2NCO$), 4.07 (4H, s, $CH_2Ph$), 7.73 (2H, t, Ph), 7.83 (2H, d, Ph), 8.30(2H, t, Ph), 8.50 (2H, d, Ph). 13C NMR (100 MHz, D20): δ 23.41 ($CH_2CH_2CO$), 28.53 ($NCH_2CH_2NCO$), 45.31 ($CH_2CH_2CO$) 47.65 (macrocycle $CH_2$), 48.27 (macrocycle $CH_2$), 49.73 (macrocycle $CH_2$), 50.27 (macrocycle $CH_2$), 52.56 (side arm $NCH_2COOH$), 53.08 (side arm $NCH_2COOH$), 54.31 ($NCH_2CH_2NCO$), 55.10 ($CH_2Ph$), 126.26 (Ph), 126.95(Ph), 141.19 (Ph), 147.27 (Ph), 152.33 (Ph), 168.38 (CO), 171.25 (COOH), 173.74 (COOH). MS (ESI): 642.79 $[M+H]^+$.

2-[4,10-bis(carboxymethyl)-7-{2-[(2-{[2-(pyridin-2-yl)ethyl](pyridin-2-ylmethyl)amino}ethyl)carbamoyl]ethyl}-1,4,7,10-tetraazacyclododecan-1-yl]acetic acid (L5) To a solution of compound 6 (0.30 g, 0.51 mmol) in DMF (2 mL) was added DIPEA (0.33 g, 2.55 mmol) and HBTU (0.39 g, 1.02 mmol). The reaction mixture was stirred at room temperature for 5 minutes. Then, compound 8 (0.33 g, 1.28 mmol) was added to the above reaction mixture and stirred at room temperature overnight. The DMF and DIPEA were both evaporated off in vacuo and the resulting solid was dissolved in deionized water. The intermediate product was extracted with dichloromethane (3×10 mL), the organic phase was dried ($Na_2SO_4$) and evaporated in vacuo to afford the intermediate as a yellow oil. The resulting oil was dissolved in a mixture of dichloromethane and TFA (10 mL: 90 mL) and stirred overnight. The solution was evaporated to give the crude product that was then purified using preparative HPLC to afford the pure ligand as a pale-yellow powder (174 mg, 0.26 mmol, 51%, two steps). 1H NMR (400 MHz, D20): δ 2.48 (2H, m, CH$_2$CH$_2$CO), 2.64 (2H, m, CH$_2$CH$_2$CO), 2.75-3.31 (16H, br, macrocycle CH$_2$), 2.88 (2H, m, NCH$_2$CH$_2$NCO), 3.25-3.38 (10H, br, CH$_2$COOH, NCH$_2$CH$_2$NCO, CH$_2$CH$_2$Ph), 3.90 (2H, m, CH$_2$CH$_2$Ph), 4.39 (2H, s, CH$_2$Ph), 7.71 (2H, d, Ph), 7.81 (1H, t, Ph), 7.86 (1H, d, Ph), 8.16 (2H, m, Ph), 8.26 (1H, d, Ph), 8.49 (1H. d, Ph). 13C NMR (100 MHz, D20): δ 28.03 (CH$_2$CH$_2$Ph), 29.26 (CH$_2$CH$_2$CO), 34.67 (NCH$_2$CH$_2$NCO), 47.48 (CH$_2$CH$_2$CO), 48.13 (CH$_2$CH$_2$Ph), 49.64 (macrocycle CH$_2$), 50.07 (macrocycle CH$_2$), 51.44 (macrocycle CH$_2$), 51.71 (macrocycle CH$_2$), 52.23 (side arm NCH$_2$COOH), 52.42 (side arm NCH$_2$COOH), 54.09 (NCH$_2$CH$_2$NCO), 54.21 (CH$_2$Ph), 125.66 (Ph), 127.40 (Ph), 128.38 (Ph), 141.22 (Ph), 143.19 (Ph), 146.15 (Ph), 146.66 (Ph), 147.16 (Ph), 147.82(Ph), 150.91 (Ph), 168.12 (CO), 171.88 (COOH), 173.55 (COOH). MS (ESI): 656.78 [M+H)]$^+$.

Scheme 8 Synthesis of L3. Reagents and conditions: (v) HBTU, DMF, DIPEA, 12hours, ii) TFA, RT, overnight (66%).

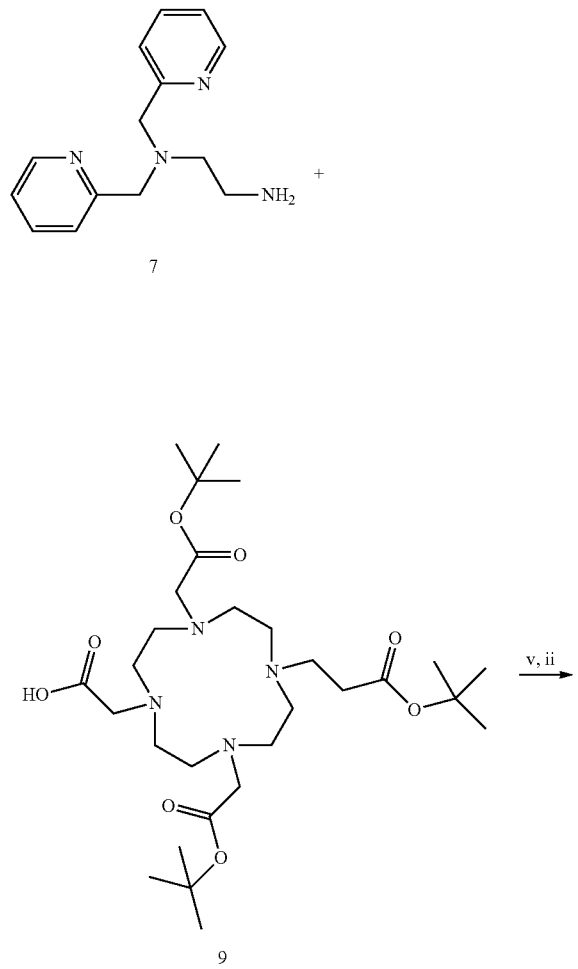

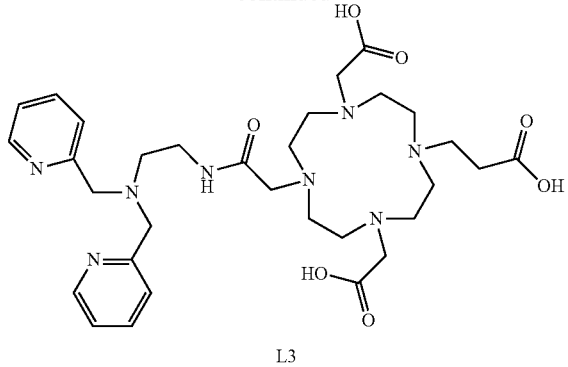

L3

3-{7-[({2-*Ibis*(pyridin-2-ylmethyl)amino]ethyl}carbamoyl)methyl]-4,10-bis(carboxymethyl)-1,4,7,10-tetraazacyclododecan-1-yl}propanoic acid (L3) Compound 9 was obtained by monoalkylation of tert-butyl 2-{7-[2-(tert-butoxy)-2-oxoethyl]-1,4,7,10-tetraazacyclododecan-1-yl}acetate(1.6 g, 3 mmol) with 1 equivalent of tert-butyl 3-bromopropanoate (0.63 g, 3 mmol) for 16h at room temperature in CH$_3$CN (100 mL) and K$_2$CO$_3$ (0.414 g, 3 mmol). The reaction was monitored by LCMS and then purified using column chromatography using silica and eluting with 10% methanol in methylene chloride to 3-{4,10-bis [2-(tert-butoxy)-2-oxoethyl]-1,4,7,10-tetraazacyclododecan-1-yl}propanoate as a colourless oil (0.9 g, 1.88 mmol, 63%). 0.9 g (1.7 mmol) of the purified compound was then reacted with 1 equivalent of benzyl bromoacetate(0.39 g, 1.7 mmol), in CH$_3$CN (100 mL) and K$_2$CO$_3$ (0.234 g, 1.7 mmol) at 60 degrees for 16 hours. K$_2$CO$_3$ was filtered off, solvent evaporated under vacuum, dissolved in CH$_2$Cl2, washed with brine, organic phase collected, dried over Mg$_2$SO$_4$ and concentrated in vacuo to give benzyl 3-{4,7,10-tris [2-(tert-butoxy)-2-oxoethyl]-1,4,7,10-tetraazacyclododecan-1-yl}propanoate (1.05 g, 1.55 mmol, 91%). The benzyl-ester group was removed by hydrogenation with Pd/C,H$_2$ for 12 hours and the mixture was purified using a preparative HPLC to yield 2-{4,10-bis [2-(tert-butoxy)-2-oxoethyl]-7-[3-(tert-butoxy)-3-oxopropyl]-1,4,7,10-tetraazacyclododecan-1-yl}acetic acid (9) as a white powder (0.8 g 1.36 mmol, 88%). MS (ESI): 587.76 [M+H]+. The title compound was obtained using similar procedures used to synthesize compound L2 and L5. $^1$H NMR (400 MHz, D20): δ 2.66 (2H, t, CH$_2$CH$_2$COOH), 2.78 (2H, t, NCH$_2$CH$_2$NCO), 2.75-3.02 (16H, br, macrocycle CH$_2$), 3.29 (2H, t, NCH$_2$CH$_2$NCO) 3.33 (4H, m, CH$_2$CO$_2$), 3.41 (2H, t, CH$_2$CH$_2$COOH), 3.93 (2H, m, NCH$_2$CH$_2$NCO), 4.10 (4H, s, CH$_2$Ph), 7.76 (2H, t, Ph), 7.87 (2H, d, Ph), 8.34(2H, t, Ph), 8.53 (2H, d, Ph). 13C NMR (100 MHz, CDCl$_3$): δ 27.79 (CH$_2$CH$_2$COOH), 36.46 (NCH$_2$CH$_2$NCO), 47.77 (CH$_2$CH$_2$COOH) 48.20 (macrocycle CH$_2$), 49.92 (macrocycle CH$_2$), 51.61 (macrocycle CH$_2$), 52.74 (macrocycle CH$_2$), 53.18 (side arm NCH$_2$COOH), 55.01 (CH$_2$Ph), 55.10 (NCH$_2$CH$_2$NCO), 126.28 (Ph), 127.01 (Ph), 141.31 (Ph), 147.26 (Ph), 152.31 (Ph), 167.62 (CO), 173.60 (COOH), 173.84 (COOH). MS (ESI): 642.76 [M+H]$^+$ Example 2—Physico-Chemical Characterization and Relaxivity Studies

TABLE 1

Relaxivities and $K_D$ values for the different sensors measured at 0.5 T and 37° C. (100 mM Tris buffer).

| | $r_1$ (s$^{-1}$ mM$^{-1}$) | | | | | | |
|---|---|---|---|---|---|---|---|
| CAs | No Zn$^{2+}$ | With Zn$^{2+}$ | 0.6 mM HSA alone | Zn$^{2+}$ + 0.6 mM HSA | $K_{D(GdLZn)}$ (nM)[e] | $K_{D(GdLZnHSA)}$ (μM)[f] | $r_1$[c] (s$^{-1}$ mM$^{-1}$)[c] |
| GdL1 | 4.8 ± 0.1 | 5.2 ± 0.1[b] | 5.8 ± 0.1 | 17.8 ± 0.5[b] | 118 ± 3 | 36 ± 1[c]  48 ± 6[d] | 20 ± 0.5 |
| GdL2 | 4.9 ± 0.1 | 5.5 ± 0.1[b] | 6.5 ± 0.1 | 19.8 ± 0.6[b] | 190 ± 5 | 37 ± 1[c]  49 ± 7[d] | 28 ± 0.3 |
| GdL3 | 5.0 ± 0.1 | 5.4 ± 0.1[b] | 6.9 ± 0.2 | 21.5 ± 0.7[b] | 185 ± 5 | 37 ± 1[c]  51 ± 7[d] | 30 ± 0.6 |
| GdL4 | 4.7 ± 0.1 | 5.1 ± 0.1[b] | 5.6 ± 0.1 | 11.4 ± 0.3[b] | 2350 ± 5 | 42 ± 1[c]  55 ± 12[d] | 12 ± 0.3 |
| GdL5 | 4.9 ± 0.1 | 5.3 ± 0.1[b] | 6.3 ± 0.2 | 10.4 ± 0.3[b] | 2567 ± 54 | 43 ± 1[c]  54 ± 1[d] | 12 ± 0.3 |
| 1* | 5.0 | 6.0[a] | 6.6 | 17.4[a] | 33.6 | 48[c]  42[d] | — |
| 2 (3)* | 6.4 (6.2) | 7.0 (7.0)[a] | 12.3 (11.6) | 47.6 (5.01)[a] | — | —  48 (42)[d] | 48 (55) |

Figure 4:
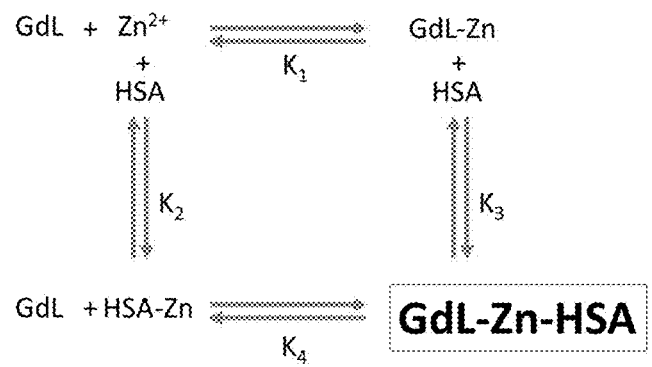
FIG. 4 shows the ternary complex equilibria for aqueous solutions containing a MRI sensor, $Zn^{2+}$ and HSA.

[a]CA:Zn = 1:2 (2 equivalents of ZN$^{2+}$).
[b]Ca:Zn = 1:1 (1 equivalent of ZN$^{2+}$).
[c]Obtained by one site competition fitting with dansylglycine.
[d]Obtained by fitting proton relaxation enhancement data to equation (1).
[e]Referred as $K_2$ in FIG. 4.
[f]Referred as $K_3$ and $K_4$ in Scheme 9
*Compounds Described Below.

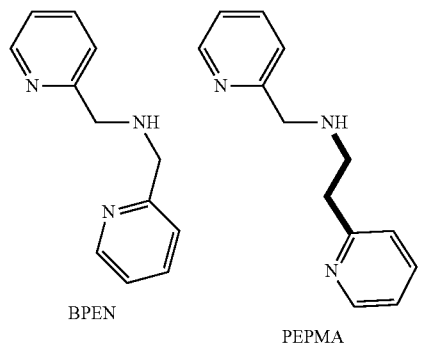

BPEN          PEPMA

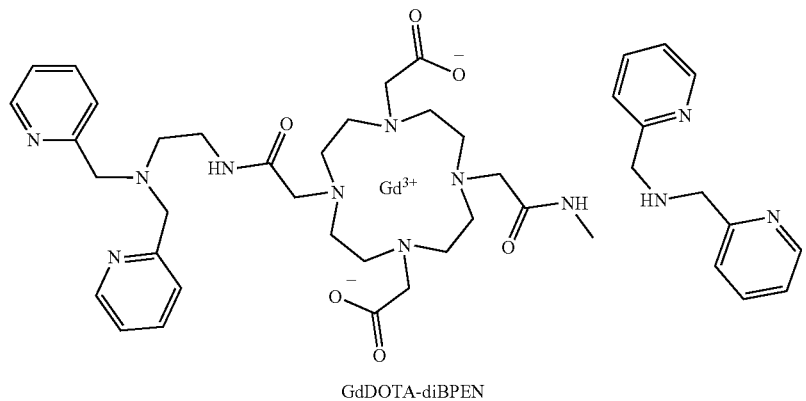

GdDOTA-diBPEN

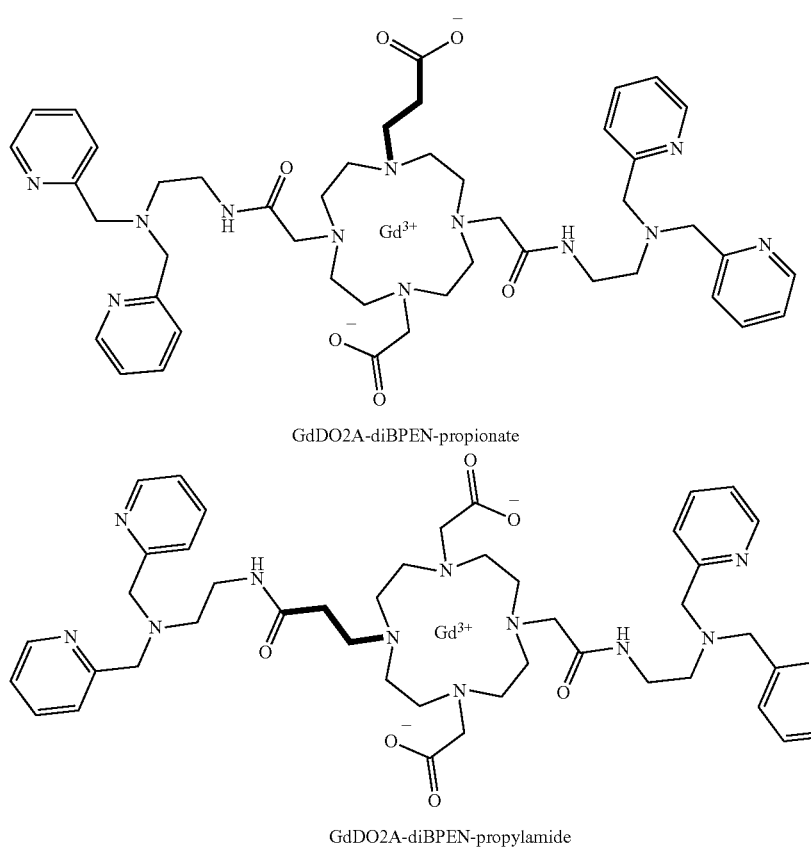

GdDO2A-diBPEN-propionate

GdDO2A-diBPEN-propylamide

The $r_1$ relaxivities of GdL1-5, their binary complexes with $Zn^{2+}$ and their ternary with $Zn^{2+}$ plus HSA are listed in Table 1. These data clearly show that the new compounds with a single BPEN chelating moiety have the same characteristics displayed by our first-generation agents, where $r_1$ increases only in the presence of both $Zn^{2+}$ and HSA. Interestingly, the magnitude of $r_1$ for GdL1, GdL2, and GdL3 in the presence of both $Zn^{2+}$ and HSA was similar to that observed for GdDOTA-diBPEN (De Leon-Rodriguez et al., 2012; Esqueda et al., 2009; Yu et al., 2015) but lower than the $r_1$ achieved in the water exchange optimized complexes (2 and 3) (Yu et al., 2015). GdL4 and GdL5 were designed to reduce the binding affinity of the agent for $Zn^{2+}$ while maintaining their HSA binding characteristics. As the data show, $r_1$ also increases after addition of $Zn^{2+}$ and HSA to GdL4-5, but here the increase in $r_1$ is about 50% less than in GdL1-3. A titration of all five complexes, GdL1-5, with $Zn^{2+}$ shows that $r_1$ increases until a 1:1 complex is formed (FIG. 1) then levels off with the further addition of $Zn^{2+}$. This observation indicates that all five complexes form 1:1 complexes with $Zn^{2+}$ with relatively high affinity.

TABLE 2

Fitted physical parameters: water exchange rates ($k_{ex}$) and hyperfine coupling constants ($A_O/\hbar$) of the corresponding GdL complexes.

| complexes | $k_{ex}^{310}$ ($\times 10^6$ s$^{-1}$) | ($A_O/\hbar$) ($\times 10^6$ rad/s) | Ref |
|---|---|---|---|
| GdL1 | 2.9 ± 0.1 | −4.0 ± 0.2 | |
| GdL2 | 100 ± 1 | −3.7 ± 0.2 | |
| GdL3 | 90 ± 0.2 | −3.7 | |
| GdL4 | 3.0 ± 0.1 | −4.0 ± 0.2 | |
| GdL5 | 100 ± 1 | −3.9 ± 0.3 | |
| GdDOTA-diBPEN | 1.1 | −3.7 | Yu et al., 2015 |
| GdDOTA$^a$ | 4.1 | −3.7 | Powell et al., 1994; Powell et al., 1996 |

$^a$Measured at 25° C. Underlined values were fixed during the fitting.

Figure 5:
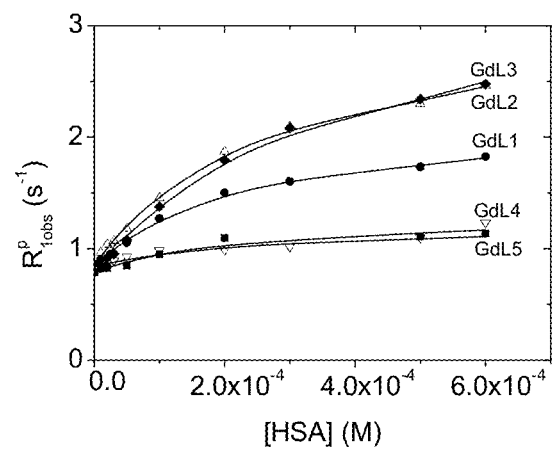
FIG. 5 shows the proton relaxation enhancement titrations of each complex (GdL1-5, 0.1 mM) as a function of increasing [HSA]. $[Zn^{2+}]$ was held constant (0.6 mM, equal to the highest concentration of HSA) in each titration. All measurements were performed at 20 MHz, 310 K in 100 mM Tris buffer at pH 7.

Given that the rate of water exchange ($k_{ex}$) in these complexes is likely the limiting factor in determining the magnitude of $r_1$ increase when the GdL-Zn complexes bind to HSA, further temperature dependent $^{17}O$ NMR studies were performed to evaluate the water exchange rates. A simultaneous analysis of $^{17}O$ reduced $T_1$, $T_2$, and chemical shift ($\Delta\omega_r$) data were analyzed (Powell et al., 1996; Gonzalez et al., 1994; Martins et al., 2013; Martins et al., 2015) to estimate the q values, $k_{ex}$, and hyperfine coupling constants for GdL1-5. These data are summarized in Table 2. Among these five complexes, GdL1 and GdL4 exhibit the slowest exchange rates ($k_{ex}\sim 3\times 10^6$ 5-1) similar to the value reported for GdDOTA. GdL2, GdL3, and GdL5 displayed ~30-fold faster water exchange rates ($k_{ex}=90-100\times 10^6$ s$^{-1}$) as expected for $Gd^{3+}$ complexes with an extra methylene carbon in one of the side-chain moeities. Nonetheless, even with nearly optimized water exchange rates, the HSA bound $r_1$ values for GdL2, GdL3, and GdL5 did not approach those of the analogous sensors having two $Zn^{2+}$ binding groups and optimized water exchange rates which have $r_1$ values approaching ~50 $s^{-1}$ $mM^{-1}$ (Yu et al., 2015) A likely reason for the lower than expected $r_1$ values of these new one-armed agents is that they may experience a different hydration environment when bound to HSA that results in either faster or slower water exchange compared to the rate measured for the unbound complex in aqueous buffer.

the these $Zn^{2+}$ sensors likely bind to HSA via electrostatic interactions between one of $Zn^{2+}$-BPEN arm and the tyrosine Y411 in pocket site 2 (FIG. 5). (Esqueda et al., 2009; Yu et al., 2015) Previously reported sensors having a single $Zn^{2+}$ pendant binding moiety display only modest increases in $r_1$ when mixed with albumin from various mammalian sources (Major et al., 2007; Mishra et al., 2011; Major et al., 2008). For the sensors reported here, the $r_1$ relaxivities also did not change significantly upon addition of one equivalent of $Zn^{2+}$ or HSA alone but did increase upon addition of both $Zn^{2+}$ and 600 μM HSA (Table 1). A 430% increase in $r_1$ was observed for agents with a high affinity for $Zn^{2+}$ (GdL1-3) but only a 240% increase in $r_1$ was found for those agents with a lower affinity for $Zn^{2+}$ (GdL4-5). These data show that all sensors reported here having a single recognition site for $Zn^{2+}$ retain their ability to bind to HSA in the presence of $Zn^{2+}$ ions similar to the previously reported GdDOTA-diBPEN derivatives (Esqueda et al., 2009; Yu et al., 2015)

TABLE 3

Best-fit parameters obtained for [Gd(sensors)(H$_2$O)] from the analysis of $^{17}$O NMR data.

| Parameters | GdDOTA-diBPEN 1 | GdL1 | GdL2 | GdL3 | GdL4 | GdL5 | GdDOTA |
|---|---|---|---|---|---|---|---|
| $\Delta H\ddagger$ [kJ/mol] | 38.0 ± 5.0 | 44.3 ± 1.0 | 45.8 ± 1.1 | 47.0 ± 1.0 | 15.1 ± 1.5 | 45.7 ± 1.3 | 49.8 |
| $E_R$ [kJ/mol] | 15.0 | 20.7 ± 0.2 | 17.1 ± 0.2 | 17.2 ± 0.1 | 17.4 ± 0.2 | 15.0 | 16.1 |
| $\tau_{RO}^{298}$ [ps] | 375 ± 11 | 280 ± 11 | 320 ± 11 | 320 | 350 ± 12 | 305 ± 10 | 77 |
| $E_V$ [kJ/mol] | 1.0 | 1.1 ± 0.1 | 1.1 ± .01 | 1.1 | 1.0 | 1.0 | 1.0 |
| $\tau_V^{298}$ [ps] | 11 | 4.6 ± 0.1 | 7.1 ± 0.1 | 7.1 | 11 | 14 ± 0.2 | 11 |
| $\Delta^2$ [$10^{20}$ $s^{-2}$] | 0.16 | 0.10 ± 0.01 | 0.13 ± 0.01 | 0.13 | 0.16 | 0.67 ± 0.2 | 0.16 |
| A/ℏ [MHz/$10^{-6}$] | −3.7 | −4.0 ± 0.1 | −3.7 ± 0.2 | −3.7 | −4.0 ± 0.4 | −3.9 ± 0.2 | −3.7 |

TABLE 4

Best-fit parameters obtained for [DyL4(H$_2$O)] from the analysis of $^{17}$O NMR data.

| Parameters | GdL2 | GdL2•HSA | Dy DOTA-(gly)$_4$ | DyDOTA |
|---|---|---|---|---|
| $k_{ex}^{298}$ ($10^6$ $s^{-1}$) | 4.3 ± 0.1 | 11 ± 0.1 | 0.09 | 70 |
| $\Delta H\ddagger$ [kJ/mol] | 41.3 ± 0.5 | 71.6 ± 0.8 | 53 | 90 |
| $1/T_{2m}^{298}$ ($10^4$ $s^{-1}$) | 600 ± 20 | 400 ± 15 | 1000 | 20 |
| $E_R$ [kJ/mol] | 40 ± 10 | 70 ± 15 | −50 | −90 |
| $A_1$ ($10^6$ rad $s^{-1}$ $K$ $T^{-1}$) | −73 ± 2 | −73 ± 2 | −50 | −50 |
| $A_2$ ($10^9$ rad $s^{-1}$ $K^2$ $T^{-1}$) | 0.3 ± 0.1 | 0.3 ± 0.1 | 0 | 0 |

Figure 3:
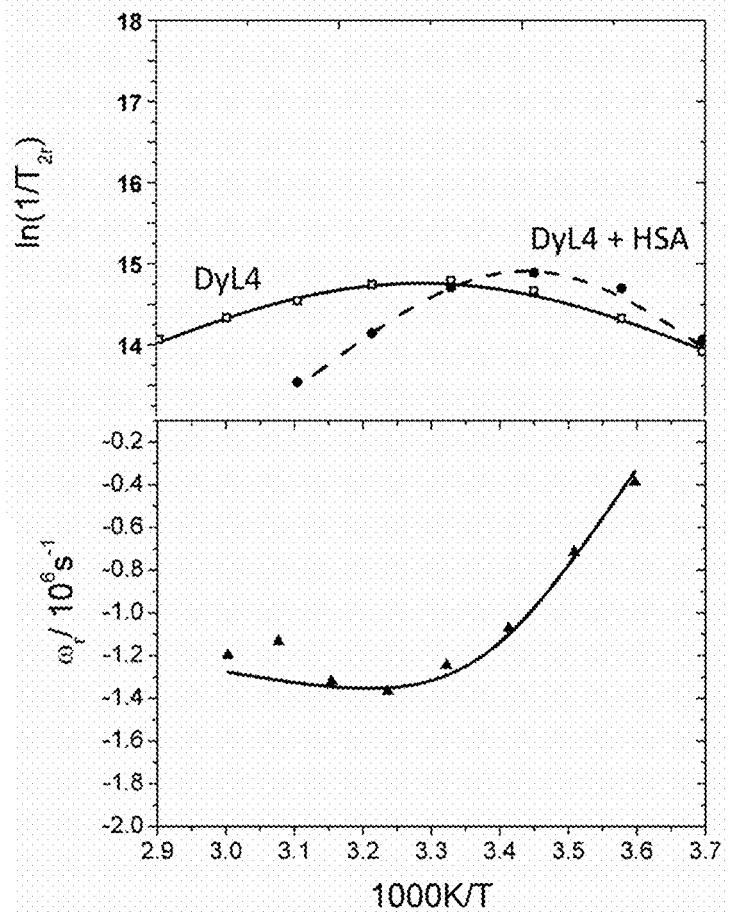
FIG. 3 shows the temperature dependence of the reduced transversal $^{17}O$ relaxation rates (top) and reduced chemical shifts (bottom). 2 mM of DyL4 in $^{17}O$ enriched water, TRIS buffered at pH 7 (solid lines) and 1 mM DyL4 with 3 mM HSA in $^{17}O$ enriched water, TRIS buffered at pH 7 (dashed line, •). $B_0$=9.4 T.

To gain more insights into this process, further $^{17}$O NMR experiments performed using DyL4 in the presence of 0.6 mM HSA ($Dy^{3+}$ was substituted for $Gd^{3+}$ for improved fitting purposes, FIGS. 2 and 3 and Table 4). An analysis of these data shows quite clearly that the rates of water exchange is about 2-3-fold faster when the complex is bound to HSA compared to free in solution. Although one cannot necessarily assume that water exchange rates are identical in DyL4 and GdL4, (Zhang et al., 2003) these data do demonstrate the water exchange rates can indeed differ when any of the agents reported here are bound to HSA.

Example 3—HSA Binding Studies

Figure 6:
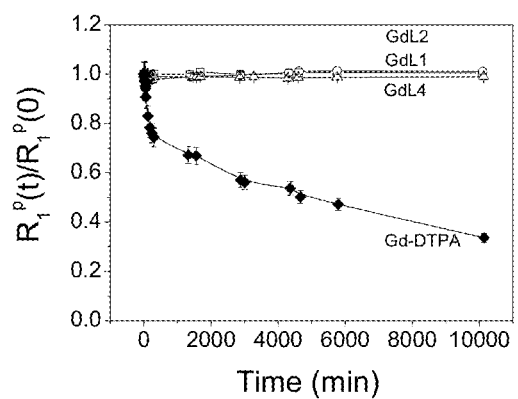
FIG. 6 shows the normalized $R_1$ rates for GdL1=□, GdL2=Δ, GdL4=○, and GdDTPA=♦ as a function of time. At time zero, each agent (1.5 mM) was dissolved in 30 mM sodium phosphate buffer (pH=7) in the presence of 6 mM of Zn(II). The samples were maintained at 310 K. The error bars reflect standard deviations.

Human serum albumin, the most abundant protein in plasma, is known to have a relatively high binding affinity for $Zn^{2+}$ ions (29.5 nM) (Stewart et al., 2003). Molecules containing a BPEN moiety also have an affinity for $Zn^{2+}$ in the nM range ($K_{D(GdDOTA-diBPEN)}$=33.6 nM) (Esqueda et al., 2009; Livieri et al., 2007) so in a complex mixture containing a Gd-based Zn sensor, HSA, and $Zn^{2+}$ ions, several species are present in solution (FIG. 4). At low-to-medium magnetic fields, $r_1$ is largely governed by the rotational correlation time, $\tau_R$, such that the $r_1$ of GdL-Zn-HSA typically dominates a measured $r_1$ value. As reported previously, Proton relaxation enhancement (PRE) titrations were performed to evaluate the binding of these agents to HSA under conditions where the concentration of HSA was varied while the concentration of GdL and $Zn^{2+}$ (1:1) were held constant (FIG. 6). These data were fit to eq.1 to obtain $r_1^f$ and $r_1^c$, the proton relaxivities of the free and the bound state, $c_{HSA}$ and $c_1$, the concentration of HSA and zinc sensor, respectively, and n, the number of binding sites on the protein. These types of complexes only bind to HSA-binding site 2 of subdomain IIIA, so n was assumed=1.

$$R_1^{pobs} = 10^3 \times \begin{Bmatrix} (r_1^f \cdot c_1) + \frac{1}{2}(r_1^c - r_1^f) \times \\ \left( n \cdot c_{HSA} + c_1 + K_A^{-1} - \sqrt{(n \cdot c_{HSA} + c_1 + K_A^{-1})^2 - 4 \cdot n \cdot c_{HSA} \cdot C_1} \right) \end{Bmatrix} \quad (I)$$

The fit of the PRE data to eqn 1 shows that all five complexes bind to HSA with affinities ($K_D$ ~48-54 μM) similar to those found previously for other GdDOTA-diBPEN derivatives (Table 1). These affinity constants were confirmed by parallel fluorescence titrations using dansylglycine, a drug site 2 competitive binding ligand. Those titrations yielded similar $K_D$ values and confirmed the strong binding of the sensors to HSA in the presence of $Zn^{2+}$. It is noteworthy also that for the first time, an accurate study of the interaction of low-affinity zinc sensors was possible, without interferences from the second BPEN unit on the same molecule (Leon-Rodriguez et al., 2012).

Example 4—Kinetic Stability of the Agents

Figures 7A, 7B, 7C:
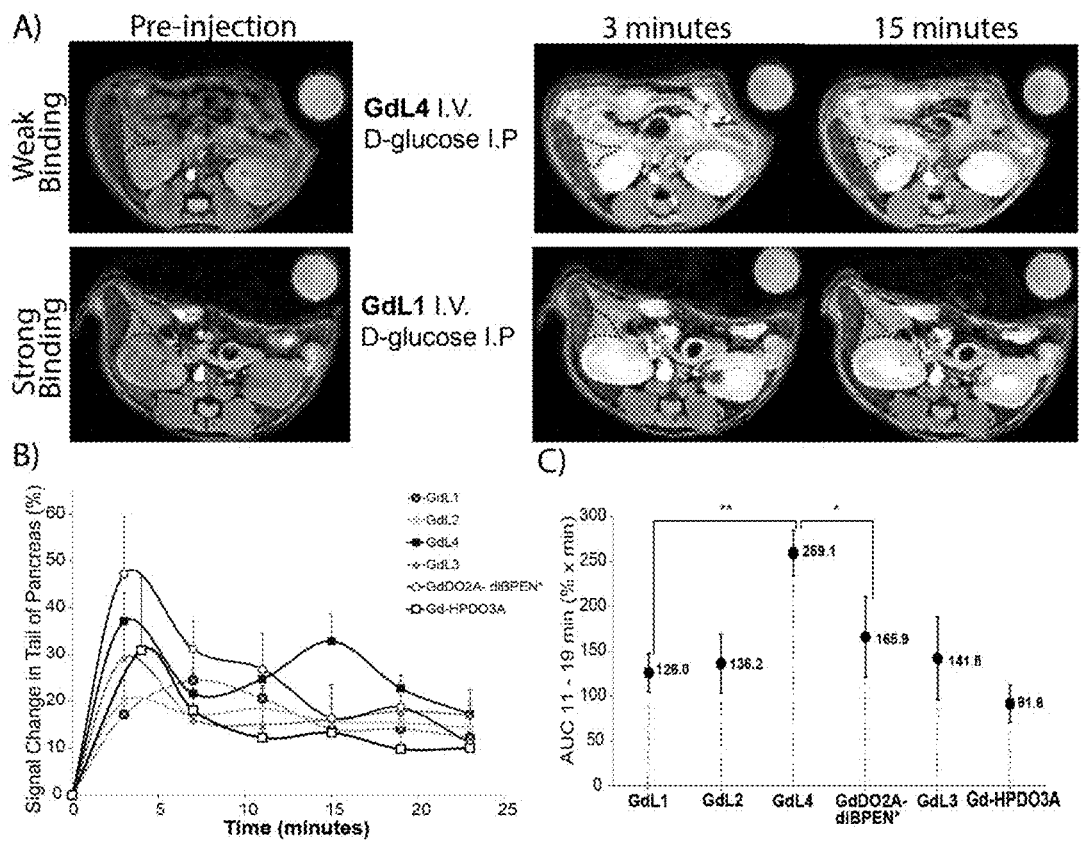
FIGS. 7A-7C shows the in vivo MR imaging and quantification of GSIS in the mouse pancreas. All $Zn^{2+}$ sensors were injected intravenously as a bolus after an intraperitoneal injection of glucose was administered to simulate insulin secretion. $T_1$-weighted images were collected sequentially for 30 minutes post-injections. The portion of the pancreas that could be identified in these slices is outlined in blue (FIG. 7A) MR images show the pancreatic response comparing imaging agents with weaker and stronger binding affinity to $Zn^{2+}$. GdL4 ($K_{D(GdLzn)}$=2350 nM) and GdL1 ($K_{D(GdLzn)}$=118 nM) both enhance the pancreas at 3 minutes, while only GdL4 shows second-phase enhancement at 15 minutes post-glucose stimulation.

Shortly after the first confirmed clinical cases of nephrogenic systemic fibrosis (NSF), increased efforts have been made to design agents with high thermodynamic stability and kinetic inertness (Kallen et al., 2008; Reilly, 2008; Rofsky et al., 2008; Wiginton et al., 2008; Abujuden et al., 2009). The sensors shown here are very stable macrocyclic DO3A-monoamide derivatives with reported log $K_{ML}$>20. However, given that the agents reported here also have a high affinity for $Zn^{2+}$ ions, and $Zn^{2+}$ has been implicated as the major competing ion for transmetalation of $Gd^{3+}$ agents derived from linear polyamine ligands, the kinetic rate of $Gd^{3+}$ release is arguably the most critical factor in determining in vivo toxicity (Laurent et al., 2010). Using a previously published method (Laurent et al., 2010) consisting of incubating each agent with four equivalents of $Zn^{2+}$ in phosphate buffer (pH=7), we compared the kinetic stability of the agents reported here with the FDA-approved agent Magnevist® (GdDTPA, cf. FIG. 7). As anticipated, the macrocyclic complexes GdL1, GdL2, and GdL4 were kinetically inert while Magnevist showed some transmetalation by $Zn^{2+}$ under these conditions.

Example 5—In Vivo Imaging of Glucose Stimulated Insulin Secretion (GSIS)

Insulin secretion from β-cells is known to occur in a biphasic pattern reflecting release of insulin granules in two distinct pools, a readily releasable pool (RRP) and a reserve pool (RP) (Dean, 1973; Rorsman et al., 2000; Olofsson et al., 2002; Komatsu et al., 2013; Wang et al., 2013) The RRP contains a small portion (<5%) of the insulin granules pre-docked or primed close to the cell membrane with the RP containing the vast majority (>95%) of insulin granules located far beneath the cell membrane that co-sediment with F-actin. The dense web of the F-actin network serves as a barrier for insulin granules in RP to reach the cell surface in the basal condition, but upon receiving a secretagogue signal, the concentration of intracellular $Ca^{2+}$ increases and this significantly reduces interactions between F-actin and the insulin granules. Both phases of insulin secretion are considered essential, but the early RRP phase that is thought to be the first signal reduced during the development of type 2 diabetes (Komatsu et al., 2013; Hosker et al., 1989). In principle, both phases of insulin secretion should be detectable by MRI if enough sensor is present in the extracellular space during the time-course of these events. Biphasic GSIS was not detected by MRI in previous experiments using the first generation $Zn^{2+}$ sensors with a high affinity for $Zn^{2+}$ but we hypothesized that GSIS may be more easily detected using these second-generation agents having a much lower affinity for $Zn^{2+}$. To test this, dynamic MRI scans were collected after administering either GdL1, GdL2, GdL3 or GdL4 to C57B1/6 mice via a tail vein (0.07 mmol/kg). Nearly simultaneously with agent injection, a bolus (50 µL) of 20% w/v glucose was administered IP to stimulate secretion of insulin. $T_1$-weighted MR images showed significant image enhancements in both pancreatic tissues and kidneys over the first 10-15 min after injection of either GdL1, GdL2, GdL3, GdDOTA-diBPEN or GdHPDO3A (serving as a control) with image intensity declining gradually thereafter. However, the dynamic images collected after GdL4 (n=3) injection differed significantly, showing both early phase (3-4 min) and late phase (13-17 min) insulin secretion. See FIG. 8. This suggests that GdL4, an agent with a lower affinity for $Zn^{2+}$, is more responsive to increases in insulin and $Zn^{2+}$ that occur over this time period.

In support of these experimental observations, a model of the dynamic equilibria that considers all possible GdL, $Zn^{2+}$, and HSA species was written in MatLab code (Described below) (Douglass et al., 2013). If one assumes that bolus injection of 0.07 mmol/kg agent yields an extracellular [GdL] of ~100 µM, extracellular [HSA] is ~600 µM, and that the concentration of $Zn^{2+}$ in the extracellular space around β-cells increases from ~50 µM to ~500 µM during release of insulin (Davis et al., 2000). With these assumptions, one can generate speciation plots such as those shown in FIG. 9. These plots show that when a low-affinity $Zn^{2+}$ agent ($K_{D(GdLzn)}$=2 µM) is used and 50 µM $Zn^{2+}$ is present (the assumed basal level), considerably more Zn-HSA is formed in comparison to GdL-Zn-HSA. However, when a high $Zn^{2+}$ affinity agent ($K_{D(GdLzn)}$=120 nM) is used, about equal amounts of Zn-HSA and GdL-Zn-HSA are formed with total $Zn^{2+}$ at 50 µM (the same basal level). The practical result of this calculation shows that the background image intensity would be considerably higher when using a high affinity $Zn^{2+}$ agent. As further $Zn^{2+}$ is released from cells, the additional amount of GdL-Zn-HSA formed with either agent reaches a maximum when $Zn^{2+}$ levels reach ~500 µM and the total amount of GdL-Zn-HSA formed is about 5-fold higher when using the high-affinity agent. See FIG. 10.

Example 6—Methods and Materials

A. Relaxivity Measurements

Longitudinal relaxation times were measured using inversion recovery method on a MRS-6 NMR analyzer from the Institute Jožef Stefan (Ljubljana, Slovenija) operating at 20 MHz. Relaxivity was determined by linear regression analysis of the relaxation rates of five solutions (0-1.0 mM). All samples were measured at 310 K using a warm air blower. Five different sample concentrations (0, 0.25, 0.5, 0.75, 1.0 mM) of gadolinium complex were made up in Tris buffer at 0.1 M and pH 7.4 to generate the relaxivity value for the free complex. $ZnCl_2$ was then added to each of the above sample to produce a [Gd]:[Zn] ratio of 1:1. After 30 min of incubation at 310 K, $T_1$ measurements were performed, from which the relaxivity of sensor-$Zn^{2+}$ was calculated. Finally, HSA was added to each of above sample to achieve HSA concentration of 0.6 mM. After further incubation at 310 K for 30 min, $T_1$ of each sensor-$Zn^{2+}$-HSA adduct was measured, from which the relaxivity of sensor-$Zn^{2+}$-HSA adduct was calculated. Zinc titrations were performed with constant [GdL]=0.5 mM and increasing amounts of [$Zn^{2+}$]=0-2 mM in Tris buffer at 0.1 M and pH 7.4.

B. $^{17}O$ NMR to Determine $\tau_M$ $^{17}O$ NMR experiments were performed at 9.4 T on a Bruker AVANCE III NMR spectrometer. The temperature was regulated by air flow controlled by a Bruker VT unit. The samples ([$Gd^{3+}$]=25 mM; [$Dy^{3+}$]=1 mM) were prepared in $^{17}O$ enriched water (10%) with the pH being maintained at 7.4 with 100 mM Tris buffer. The sample was loaded into a 18 µL spherical bulb (Wilmad-Lab Glass, Vineland, NJ) and placed inside a 5 mm NMR tube containing 400 µL of water to eliminate any susceptibility effects. Longitudinal relaxation rates (1/$T_1$) were obtained by the inversion recovery method and transverse relaxation rates (1/$T_2$) were obtained by the Carr-Purcell—Meiboom—Gill spin echo technique. The acidified water (pH=3.0) containing 10% enriched $^{17}$O water was used as a reference for the measurements. For the DyL4 complexes (no HSA and with HSA+Zinc), acidified water solutions and 1 mM LaL4+3 mM HSA with zinc (1:1) were used as the corresponding references. The corresponding fittings were performed with the Scientist 3.0 software (Micromath®).

C. Determination of GdLZn Affinity Constants to HSA

Affinity constants to HSA were assessed by proton relaxation enhancement (PRE) measurements according to published procedures (Martins et al., 2013a; Martins et al., 2013b) The proton relaxation rates at increasing concentrations of protein were measured with a MRS-6 NMR analyzer (20 MHz, 310 K). For the E-titration, the concentrations of GdL complex (0.1 mM) and Zn(II) (0.1 mM) were kept constant, while the protein concentration was varied from 0 to 0.6 mM.

D. Measurements to Determine Kinetic Inertness

Kinetic inertness was determined according to published procedures with minor modifications (Laurent et al., 2010; Silverio et al., 2009). Stock solutions of phosphate buffer (67 mM, pH=7.4), Gd(III) chelates (10 mM) and ZnCl$_2$ (231 mM) were prepared first. Calculated volumes of stock solutions or water were pipetted into small vials to obtain a test solution of 300 μL with 30 mM phosphate, 1.5 mM Gd(III) chelate, and 6.0 mM Zn(II). Samples were measured 15 minutes after the sample temperature stabilized at 310 K. During the entire experiment, the samples inside the NMR tubes were kept in an incubator at 310 K. The T$_1$ of the solutions was determined at 310 K and 0.47 T (20 MHz) at various time points within 7 days. As a reference, GdDTPA was analyzed under the same conditions. The R$_1^P$ relaxation rate is obtained by subtracting the diamagnetic contribution of the water relaxation (0.28 s-1) from the observed relaxation rate R$_1$=(1/T$_1$).

E. Data Analysis for $^{17}$O NMR Spectroscopy $^{17}$O NMR data have been analyzed within the framework of Solomon-Bloembergen-Morgan theory.

From the measured $^{17}$O NMR relaxation rates and angular frequencies of the paramagnetic solutions, 1/T$_1$, 1/T$_2$ and ω, and of the acidified water reference, a1/T$_{1A}$, 1/T$_{2A}$ and ω$_A$, one can calculate the reduced relaxation rates and chemical shifts, 1/T'2, and Δω$_r$, which may be written in Equations (A1)-(A3), where, 1/T$_{1m}$, 1/T$_{2m}$, is the relaxation rate of the bound water and Awn, is the chemical shift difference between bound and bulk water molecules, τ$_m$ is the mean residence time or the inverse of the water exchange rate k$_{ex}$ and P$_m$ is the mole fraction of the bound water (Swift and Connick, 1962; Zimmerman and Brittin, 1957).

$$\frac{1}{T_{1r}} = \frac{1}{P_m}\left[\frac{1}{T_1} - \frac{1}{T_{1A}}\right] = \frac{1}{T_{1m} + \tau_m} + \frac{1}{T_{1os}} \tag{A1}$$

$$\frac{1}{T_{2r}} = \frac{1}{P_m}\left[\frac{1}{T_2} - \frac{1}{T_{2A}}\right] = \frac{1}{\tau_m}\frac{T_{2m}^{-2} + \tau_m^{-1}T_{2m}^{-1} + \Delta\omega_m^2}{(\tau_m^{-1} + T_{2m}^{-1})^2 + \Delta\omega_m^2} + \frac{1}{T_{2os}} \tag{A2}$$

$$\Delta\omega_r = \frac{1}{P_m}(\omega - \omega_A) = \frac{\Delta\omega_m}{(1 + \tau_m T_{2m}^{-1})^2 + \tau_m^2\Delta\omega_{os}^2} + \Delta\omega_{os} \tag{A3}$$

The outer sphere contributions to the $^{17}$O relaxation rates 1/T$_{1OS}$ and 1/T$_{2OS}$ are being neglected according to previous studies (Micskei et al., 1993). Therefore, Equations (A1-A2) can be further simplified to Equations (A4) and (A5):

$$\frac{1}{T_{1r}} = \frac{1}{T_{1m} + \tau_m} \tag{A4}$$

$$\frac{1}{T_{2r}} = \frac{1}{T_{2m} + \tau_m} \tag{A5}$$

The exchange rate is supposed to obey the Eyring Equation. In Equation (A6) ΔS$^‡$ and ΔH$^‡$ are the entropy and enthalpy of activation for the water exchange process, and k$_{ex}^{298}$ is the exchange rate at 298.15 K.

$$\frac{1}{\tau_m} = \tag{A6}$$

$$k_{ex} = \frac{k_B T}{h}\exp\left\{\frac{\Delta S^\ddagger}{R} - \frac{\Delta H^\ddagger}{RT}\right\} = \frac{k_{ex}^{298}T}{298.15}\exp\left\{\frac{\Delta H^\ddagger}{R}\left(\frac{1}{298.15} - \frac{1}{T}\right)\right\}$$

In the transverse relaxation, the scalar contribution, 1/T$_2$s, is the most relevant [Equation (A7)]. 1/τ$_{s1}$ is the sum of the exchange rate constant and the electron spin relaxation rate [Equation (A8)].

$$\frac{1}{T_{2m}} \cong \frac{1}{T_{2sc}} = \frac{S(S+1)}{3}\left(\frac{A}{h}\right)^2\left(\tau_{s1} + \frac{\tau_{s2}}{1 + \omega_S^2\tau_{s2}^2}\right) \tag{A7}$$

$$\frac{1}{\tau_{s1}} = \frac{1}{\tau_m} + \frac{1}{T_{1e}} \tag{A8}$$

The $^{17}$O longitudinal relaxation rates in Gd$^{3+}$ solutions are the sum of the contributions of the dipole-dipole (dd) and quadrupolar (q) mechanisms as expressed by Equations (A11-A13) for non-extreme narrowing conditions, where γ$_S$ is the electron and γ$_1$ is the nuclear gyromagnetic ratio (γ$_S$=1.76×10$^{11}$ rad s$^{-1}$ T$^{-1}$, γ$_1$=−3.626×107 rad s$^{-1}$ T$^{-1}$), r$_{GdO}$ is the effective distance between the electron charge and the $^{17}$O nucleus, I is the nuclear spin (5/2 for $^{17}$O), x is the quadrupolar coupling constant and η is an asymmetry parameter:

$$\frac{1}{T_{1m}} = \left[\frac{2}{5}\left(\frac{\mu_0}{4\pi}\right)^2\frac{\eta^2\gamma_I^2\gamma_S^2}{r^6}S(S+1) + \frac{3\pi^2}{10}\frac{2I+3}{I^2(2I-1)}\chi^2(1+\eta^2/3)\right]\tau_c \tag{A9}$$

with:

$$\frac{1}{T_{1dd}} = \frac{2}{15}\left(\frac{\mu_0}{4\pi}\right)^2\frac{\eta^2\gamma_I^2\gamma_S^2}{r_{GdO}^6}S(S+1) \times [3J(\omega_I; \tau_{d1}) + 7J(\omega_S; \tau_{d2})] \tag{A10}$$

$$\frac{1}{T_{1q}} = \frac{3\pi^2}{10}\frac{2I+3}{I^2(2I-1)}\chi^2(1+\eta^2/3) \times [0.2J_1(\omega_I) + 0.8J_2(\omega_I)] \tag{A11}$$

In Equation (A3) the chemical shift of the bound water molecule, Δω$_m$, depends on the hyperfine interaction between the Gd$^{3+}$ electron spin and the $^{17}$O nucleus and is directly proportional to the scalar coupling constant, A/h, as expressed in Equation (A12) (Brittain and Desreux, 1984).

$$\Delta\omega_m = \frac{g_L\mu_B S(S+1)B}{3k_B T}\frac{A}{\eta} \tag{A12}$$

The isotopic Landé g factor is equal to 2.0 for the Gd$^{3+}$, B represents the magnetic field, and kB is the Boltzmann constant. The outer-sphere contribution to the chemical shift is assumed to be linearly related to Acorn by a constant GUS [Equation (A13)] (Gonzalez et al., 1994).

$$\Delta\omega_{os} = C_{os}\Delta\omega_m \tag{A13}$$

With $Dy^{3+}$ solutions the correlation time for dipolar relaxation is governed by the electron spin relaxation time $T_e$ which is much shorter than $T_m$ and $\tau_R$. For this reason, $^{17}O$ transversal relaxation rates predominantly originates from Curie spin relaxation (Caravan et al., 2001; Karimi and Helm, 2016). The Curie relaxation is described by Fries (Vigouroux et al., 1999) and simplified by the Swift-Connick equations (Swift and Connick, 1962):

$$\frac{1}{T_{2ex}}\frac{1}{P_m} = \frac{1}{T_{2r}} = \left(\frac{1}{\tau_m}\right)\frac{T_{2m}^{-2} + \tau_m^{-1}T_{2m}^{-1} + (\Delta\omega_m)^2}{(\tau_m^{-1} + T_{2m}^{-1})^{-2} + (\Delta\omega_m)^2} \quad (A14)$$

The water exchange rates $k_{ex}$ and the chemical shift differences (inner-sphere water and bulk water) $\Delta\omega_m$ can be expressed as:

$$\frac{1}{\tau_m} = k_{ex} = \frac{k_{ex}^{298}T}{298.15}\exp\left[\frac{\Delta H^{\ddagger}}{R}\left(\frac{1}{298.15} - \frac{1}{T}\right)\right] \quad (A15)$$

$$\frac{1}{T_{2m}} = \frac{1}{T_{2m}^{298}}\exp\left[\frac{E_m}{R}\left(\frac{1}{298.15} - \frac{1}{T}\right)\right] \quad (A16)$$

$$\Delta\omega_m = \Delta\omega_m^{con} + \Delta\omega_m^{pseudo} = \left[\frac{C_1}{T} + \frac{C_2^2}{T^2}\right]B \quad (A17)$$

C1 and C2 are empirical constants described by Lewis and Bleaney (1972), and represent the relative contributions of the contact and pseudocontact terms. B is the external magnetic field.

ii. Analysis Details

In the $^{17}O$ NMR data fitting for the $Gd^{3+}$ complexes, $r_{GdO}$ has been fixed to 2.50 Å, based on available crystal structures and recent electron spin-echo envelope modulation (ESEEM) results (Raitsimring et al., 2004). The quadrupolar coupling constant, x $(1+1/2/3)_{1/2}$, has been set to the value for pure water, 7.58 MHz0 The following parameters have been adjusted: the water exchange rate, $k_{ex}^{298}$, the activation enthalpy for water exchange, $\Delta H^{\ddagger}$, the scalar coupling constant, A/h, the rotational correlation time ($\tau_R^{298}$) and its activation energy, ER. The parameters characterizing the electron spin relaxation, such as the correlation time for the modulation of the zero-field-splitting, $\tau_v^{298}$, and its activation energy, $E_v$, and the mean-square zero-field-splitting energy, A2 were sometimes fixed to 11 ps, 1 kJ $mol^{-1}$ and $0.16 \times 10^{-20}$ $s^{-1}$, respectively, for simpler analogy as reported for various Gd-DOTA derivatives (Powell et al., 1996). The empirical constant describing the outer sphere contribution to the $^{17}O$ chemical shift, $C_{os}$, was also fitted for complexes GdL2 (0.1) and GdL3 (0.1) otherwise small A/h values were obtained. $C_{os}$ was fixed to 0 for the remaining complexes (Powell et al., 1996). The number of inner sphere water molecules were adjusted to the values calculated by $^{17}O$ NMR for each complex (Djanashvili and Peters, 2007).

F. Determination of GdL-Zn Dissociation Constants by Fluorescence

The procedures reported by Esqueda et al were followed (Esqueda et al., 2009). Solutions containing 1 µM of ZnAF-2F, 0.05 µM $ZnCl_2$ and 100 µM GdL sensors were prepared in TRIS buffer. Aliquots of this solution were 3-fold diluted serially 10 times by addition of a buffered solution containing the same concentration of ZnAF-2F and $ZnCl_2$ but no agent. The fluorescence was measured in triplicate in 96 well plates (100 µL). In a similar manner solutions containing agent, $ZnCl_2$ but no fluorescent probe, were prepared and fluorescence measured by triplicate to account for any signal coming from the agent interacting with $Zn^{2+}$. The excitation and emission wavelengths used were 492 and 514 nm, respectively. The Zn dissociation constant was determined by fitting the data to the following equations:

$$F = F_{min} + \frac{F_{max} - F_{min}}{1 + 10^{log[GdL]_0 - logIC50}} \quad (A18)$$

$$IC50 = K'_D\left(1 + \frac{[FP]_0}{K_D}\right) \quad (A19)$$

F is the measured corrected fluorescence.
$F_{min}$ is the minimal fluorescence observed in the competition binding experiment.
$F_{max}$ corresponds to the fluorescence in absence of competitor.
$[GdL]_o$ is the concentration of the zinc sensor chosen.
IC50 corresponds to the concentration of competitor that decreases by 50% the % F.
K'D is the dissociation constant of the competitor.
$[FP]_o$ is the total concentration of the fluorescent probe.
$K_D$ is the dissociation constant of the fluorescent probe and $Zn^{2+}$. For ZnAF-2F a $K_D$ of 5.5 nM was used as reported in the literature (Martins et al., 2013).

G. Determination of GdL-Zn Dissociation Constants by Fluorescence

The procedures reported by Esqueda et al were followed (2009). A solution containing 5 µM of dansylglycine (or warfarin), 5 µM HSA, 400 µM GdL plus one equivalent of $Zn^{2+}$ was prepared in TRIS buffer. Aliquots of this solution were 2-fold diluted serially ten times by addition of a solution which contained the same concentrations of dansylglycine (warfarin) and HSA but no agent. The fluorescence of 100 µL aliquots was measured in triplicate in 96 well plates. In a similar manner solutions containing agent, HSA but no dansylglycine (warfarin), were also included. Four 100 µL aliquots of the solution containing no agent (maximum fluorescent intensity) were also measured in the same 96 well plate, along with four 100 µL aliquots of HSA in buffer.

The excitation and emission wavelengths used for the dansylglycine: 360 and 465 nm, respectively. The excitation and emission wavelengths used for warfarin: 320 and 380 nm, respectively. The HSA dissociation constant was determined using the same equations above using a $K_D$ for dansylglycine of 2.5 µM.5 Fitting was done with OriginPro8 from OriginLab Corporation.

H. In vivo Imaging of the Pancreas in Mice

All animal experiments were performed in accordance with guidelines set by the UT Southwestern Institutional Animal Care and Use Committee (IACUC). Male C57b1/6 mice were fasted for at least 12 hours before imaging experiments. The animals were anaesthetized with isofluorane and catheterized via the tail vein. Once the animals were secured inside a 38 mm volume coil, the pancreas was positioned in the center of the 9.4 T Varian MRI scanner. Two 3D T1-weighted gradient echo pre-injection scans were obtained (TE/TR=1.69/3.34 ms, NEX8, Matrix=128×128 ×128). 70 µl of 20 mM contrast agent were injected i.v. and 50 µl of 20% w/v D-glucose were injected intraperitoneally and consecutive 3D T1-weighted scans were obtained sequentially to monitor signal enhancement in the pancreas. Identification of the pancreas was accomplished by locating the tissues surrounded by the spleen, stomach, and kidneys. A total of 3 animals were scanned per group and images were quantified and analyzed using ImageJ (National Institutes of Health, Bethesda, Md.). The signal intensities from ROIs of the tip of the pancreas were measured before, at every ~3-4 minutes post D-glucose injection over 30 minutes total. The values were normalized to the signal intensity obtained from a water phantom placed on the mouse abdomen. Contrast enhancement was calculated using the formula $$\left(\frac{S_{post-injection}}{S_{pre-injection}} - 1\right) \times 100\%.$$

Statistical analysis was performed by comparing the mean values using a two-tailed t-test. Statistical difference was evaluated using t-scores and p-values at a 95 and 99% confidence level.

I. Molecular Modeling

Geometry optimizations were performed using the Chemaxon MarvinSketch 6.2.0, Molecular Mechanics force field MMFF94. Optimization was carried out using the velocity verlet integrator in 1000 steps. Atom constrains and parameterization were performed as reported before (Esqueda et al., 2009).

* * * * * * * * * * * * * * * * * * *

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

E. REFERENCES

The following references, to the extent that they provide exemplary procedural or other details supplementary to those set forth herein, are specifically incorporated herein by reference.

Abujudeh et al., J. Magn. Reson. Imaging, 30, 1335, 2009.
Bleaney, J. Magn. Reson., 8:91-100, 1972.
Brittain and Desreux, Inorg. Chem., 23:4459-4466, 1984.
Caravan et al., Magn. Reson. Med., 46:917-922, 2001.
Davis et al., Am. J. Clin. Nutr., 71, 781, 2000.
De Leon-Rodriguez et al., Inorganica Chim. Acta., 393: 12, 2012.
De Leon-Rodriguez et al., MedChemComm., 3, 480, 2012.
Dean, P. M. Diabetologia, 9, 115, 1973.
Djanashvili and Peters, Contrast Media Mol. Imaging, 2:67-71, 2007.
Douglass et al., J. Am. Chem. Soc., 135, 6092, 2013.
Esqueda, et al., J. Am. Chem. Soc., 131:11387-11391, 2009.
Gonzalez et al., J. Phys. Chem., 98:53-59, 1994.
Handbook of Pharmaceutical Salts: Properties, and Use, Stahl and Wermuth Eds.), Verlag Helvetica Chimica Acta, 2002.
Hosker et al., Metabolism, 38, 767, 1989.
Kallen et al., Am. J. Kidney Dis., 51, 966, 2008.
Karimi and Helm, Inorg. Chem., 2016.
Komatsu et al., J. Diabetes Investig., 4, 511, 2013.
Laurent et al., Contrast Media Mol. Imaging, 5:305-308, 2010.
Livieri et al., Chem. Weinh. Bergstr. Ger., 13, 2246, 2007.
Major et al., Inorg. Chem., 47, 10788, 2008.
Major et al., Proc. Natl. Acad. Sci., USA, 104:13881, 20007.
March's Advanced Organic Chemistry: Reactions, Mechanisms, and Structure, 2007.
Martins et al., ACS Med. Chem. Lett. 5:436-440, 2013b.
Martins et al., J. Biol. Inorg. Chem. 19:281-295, 2013a.
Martins et al., JBIC J. Biol. Inorg. Chem., 1, 2015.
Micskei et al., Inorg. Chem., 32:3844-3850, 1993.
Mishra et al., Chem.— Eur. J., 17, 1529, 2011.
Olofsson et al., Pflug. Arch., 444, 43, 2002.
PCT Application WO 2002/043775
PCT Application WO 2015/142583
Powell et al., J. Alloys Compd., 207-208, 20, 1994.
Powell et al., J. Am. Chem. Soc., 118:9333-9346, 1996.
Raitsimring et al., J. Phys. Chem. A, 108:7318-7323, 2004.
Reilly, R. F. Clin. J. Am. Soc. Nephrol., 3 (3), 747, 2008.
Rofsky et al., Radiology, 247, 608, 2008.
Rorsman et al., Physiology, 15, 72, 2000.
Silverio et al., Dalton Trans., 4656-4670, 2009.
Stewart et al., Proc. Natl. Acad. Sci. U.S.A, 100, 3701, 2003.
Swift and Connick, J. Chem. Phys., 37:307-320, 1962.
U.S. Patent Publication No. 2011/0009605
Vigouroux et al., Eur. Phys. J. —At. Mol. Opt. Plasma Phys., 5:243-255, 1999.
Wang et al., Diabetol. Metab. Syndr., 5, 40, 2013.
Wiginton et al., Am J Roentgenol, 190, 1060, 2008.
Yu et al., J. Am. Chem. Soc., 137, 14173, 2015.
Zhang et al., Acc. Chem. Res., 36, 783, 2003.
Zimmerman and Brittin, J. Phys. Chem., 61:1328-1333, 1957.

What is claimed is:

1. A compound of the formula:

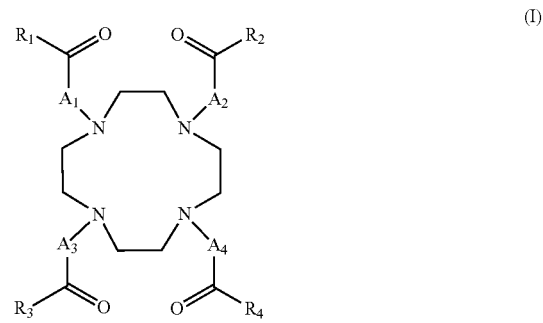

(I)

wherein:
$A_1$, $A_2$, $A_3$, and $A_4$ are each independently C1-C4 alkanediyl or substituted C1-C4 alkanediyl; and $R_2$, $R_3$, and $R_4$ are each independently hydroxy, amino, C1-C12 alkylamino, substituted C1-C12 alkylamino, C1-C12 dialkylamino, or substituted C1-C12 dialkylamino;

$R_1$ is

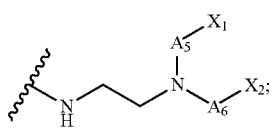

wherein:
   $A_5$ and $A_6$ are each independently C1-C4 alkanediyl or substituted C1-C4 alkanediyl; and
   $X_1$ and $X_2$ are each independently C1-C12 heteroaryl or substituted C1-C12 heteroaryl;
provided that at least one of $A_1$, $A_2$, $A_3$, $A_4$, $A_5$, and $A_6$ is not —CH$_2$—;
or a metal complex, a deprotonated form, or a salt thereof.

2. The compound of claim 1 further defined as:

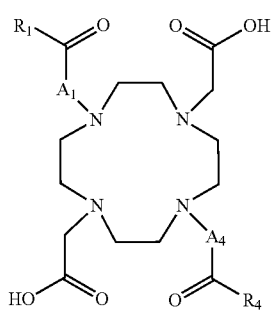

(II)

wherein:
   $A_1$ and $A_4$ are each independently C1-C4 alkanediyl or substituted C1-C4 alkanediyl; and
   $R_4$ is hydroxy, amino, C1-C12 alkylamino, substituted C1-C12 alkylamino, C1-C12 dialkylamino, or substituted C1-C12 dialkylamino;
$R_1$ is

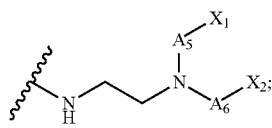

wherein:
   $A_5$ and $A_6$ are each independently C1-C4 alkanediyl or substituted C1-C4 alkanediyl; and
   $X_1$ and $X_2$ are each independently C1-C12 heteroaryl or substituted C1-C12 heteroaryl;
provided that at least one of $A_1$, $A_4$, $A_5$, and $A_6$ is not —CH$_2$—;
or a metal complex, a deprotonated form, or a salt thereof.

3. The compound of claim 2 further defined as:

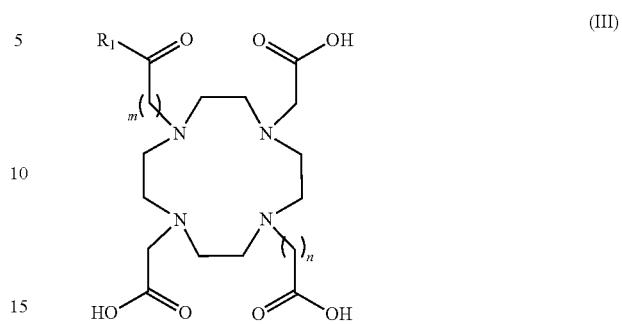

(III)

wherein:
   m and n are each independently 1 or 2; and
   $R_1$ is

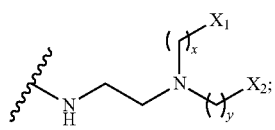

wherein:
   x and y is 1 or 2; and
   $X_1$ and $X_2$ are each independently C1-C12 heteroaryl or substituted C1-C12 heteroaryl;
provided that at least one of m, n, x, and y is not 1;
or a metal complex, a deprotonated form, or a salt thereof.

4. The compound of claim 1, wherein $A_1$ is C1-C3 alkanediyl.

5. The compound of claim 1, wherein $A_2$, $A_3$, $A_5$, and $A_6$ are C1-C3 alkanediyl.

6. The compound of claim 1, wherein $A_4$ is C1-C3 alkanediyl.

7. The compound of claim 1, wherein $R_2$, $R_3$, and $R_4$ are hydroxy.

8. The compound of claim 1, wherein $X_1$ and $X_2$ are C1-C12 heteroaryl.

9. The compound of claim 1, wherein the compound is further defined as:

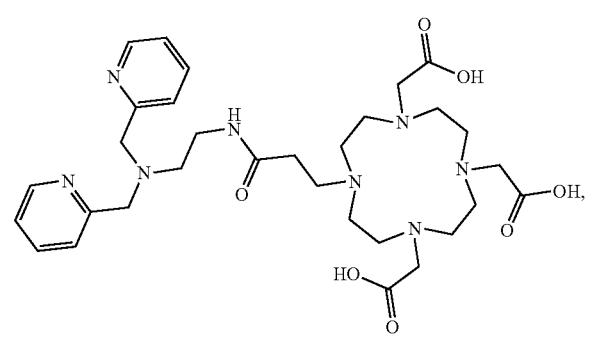

-continued

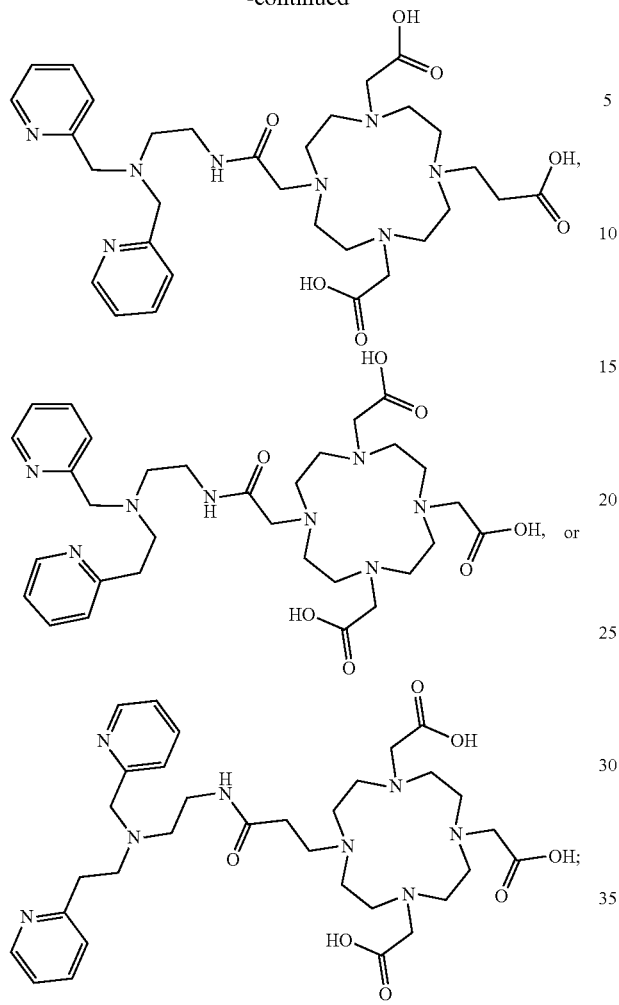

or a deprotonated form or salt thereof.

10. The compound of claim 1, wherein the compound is further defined as a metal complex of the formula:

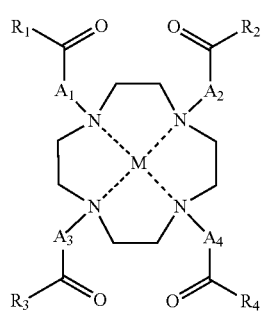
(I)

wherein:

$A_1$, $A_2$, $A_3$, and $A_4$ are each independently C1-C4 alkanediyl or substituted C1-C4 alkanediyl; and $R_2$, $R_3$, and $R_4$ are each independently hydroxy, amino, C1-C12 alkylamino, substituted C1-C12 alkylamino, C1-C12 dialkylamino, or substituted C1-C12 dialkylamino;

$R_1$ is

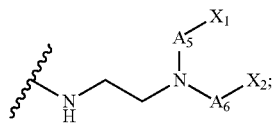

wherein:

$A_5$ and $A_6$ are each independently C1-C4 alkanediyl or substituted C1-C4 alkanediyl; and $X_1$ and $X_2$ are each independently C1-C12 heteroaryl or substituted C1-C12 heteroaryl;

provided that at least one of $A_1$, $A_2$, $A_3$, $A_4$, $A_5$, and $A_6$ is not —$CH_2$—;

or a deprotonated form or a salt thereof.

11. The compound of claim 10, wherein the metal complex is further defined by the formula:

wherein:

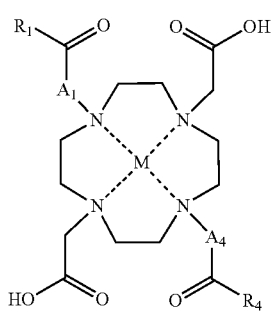
(V)

$A_1$ and $A_4$ are each independently C1-C4 alkanediyl or substituted C1-C4 alkanediyl; and $R_4$ is hydroxy, amino, C1-C12 alkylamino, substituted C1-C12 alkylamino, C1-C12 dialkylamino, or substituted C1-C12 dialkylamino;

$R_1$ is

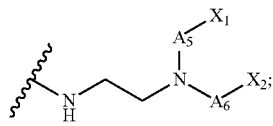

wherein:

As and A6 are each independently C1-C4 alkanediyl or substituted C1-C4 alkanediyl; and $X_1$ and $X_2$ are each independently C1-C12 heteroaryl or substituted C1-C12 heteroaryl;

provided that at least one of A1, A4, As, and A6 is not —$CH_2$—;

or a deprotonated form or a salt thereof.

12. The compound of claim 11, wherein the metal complex is further defined by the formula:

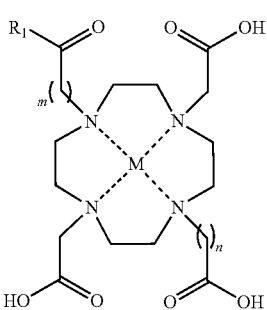

(VI)

wherein:
 m and n are each independently 1, 2, 3, or 4; and
 $R_1$ is

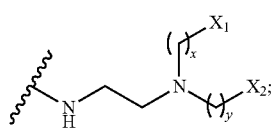

wherein:
 x and y is 1, 2, 3, or 4; and
 $X_1$ and $X_2$ are each independently C1-C12 heteroaryl or substituted C1-C12 heteroaryl;
provided that at least one of m, n, x, and y is 1;
or a deprotonated form, or a salt thereof.

13. The compound of claim 1, wherein the compound is further defined as:

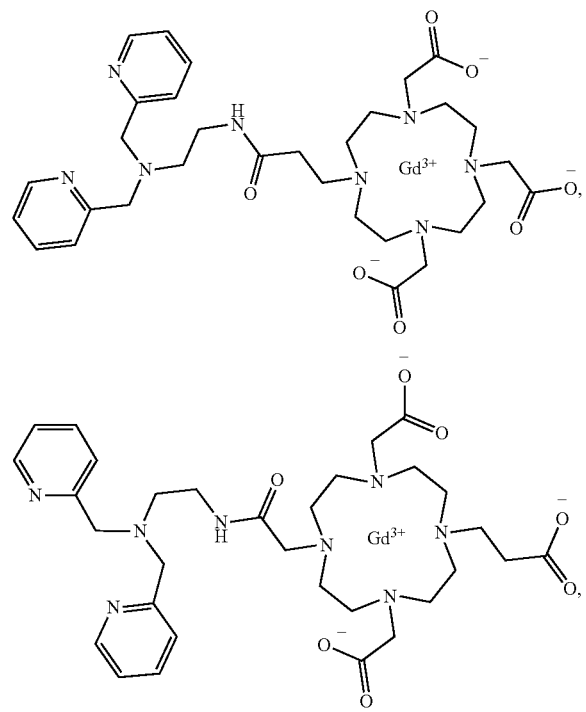

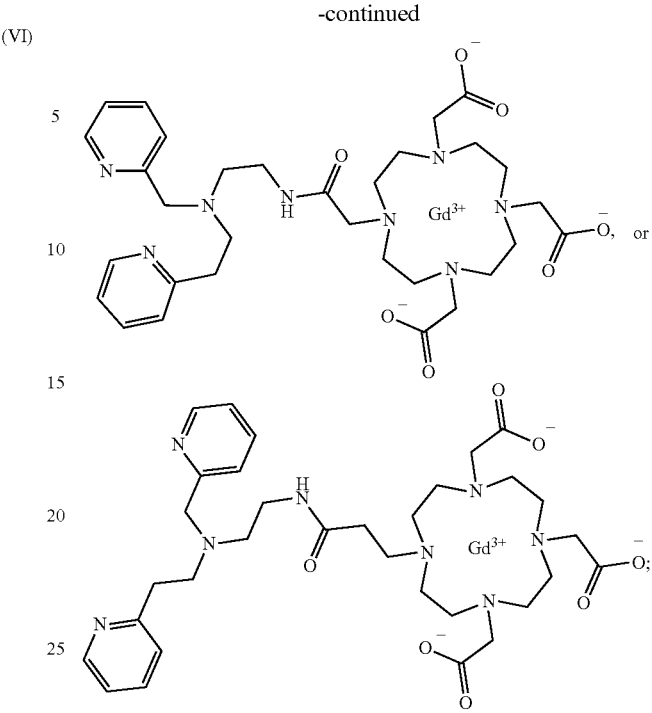

or a deprotonated form or salt thereof.

14. A pharmaceutical composition comprising:
 (A) a compound of claim 1; and
 (B) an excipient.

15. A method of imaging the pancreas in vivo in a patient to determine the onset of β-cell degeneration comprising the steps of:
 (A) administering to the patient a compound of claim 1;
 (B) obtaining an imaging scan of the patient; and
 (C) determining the presence of $Zn^{2+}$ ions by analyzing the imaging scan of the patient to determine the presence of $Zn^{2+}$ ions.

16. A method of imaging the prostate in vivo in a patient to determine the presence of a prostate tumor comprising the steps of:
 (A) administering to the patient a compound of claim 1;
 (B) obtaining an imaging scan of the patient; and
 (C) determining the presence of $Zn^{2+}$ ions by analyzing the imaging scan of the patient to determine the presence of $Zn^{2+}$ ions.

17. A method of imaging the pancreas in vivo in a patient to determine the secretion of insulin comprising the steps of:
 (A) administering to the patient a compound of claim 1;
 (B) obtaining an imaging scan of the patient; and
 (C) determining the presence of $Zn^{2+}$ ions by analyzing the imaging scan of the patient to determine the presence of $Zn^{2+}$ ions.

* * * * *

UNITED STATES PATENT AND TRADEMARK OFFICE
CERTIFICATE OF CORRECTION

PATENT NO. : 11,713,305 B2
APPLICATION NO. : 16/026340
DATED : August 1, 2023
INVENTOR(S) : Andre F. Martins et al.

It is certified that error appears in the above-identified patent and that said Letters Patent is hereby corrected as shown below:

In the Claims

In Claim 1, Column 49, Line 16, delete "As and A6" and insert -- $A_5$ and $A_6$ -- therefor.

In Claim 11, Column 52, Line 57, delete "As and A6" and insert -- $A_5$ and $A_6$ -- therefor.

Signed and Sealed this
Nineteenth Day of September, 2023

*Katherine Kelly Vidal*
Katherine Kelly Vidal
*Director of the United States Patent and Trademark Office*